(12) United States Patent
Linnes et al.

(10) Patent No.: US 11,633,152 B2
(45) Date of Patent: Apr. 25, 2023

(54) METHOD OF MONITORING RESPIRATORY RATE IN A HEALTH MONITORING DEVICE

(71) Applicant: Purdue Research Foundation, West Lafayette, IN (US)

(72) Inventors: Jacqueline C Linnes, West Lafayette, IN (US); Benjamin David Walters, Castle Rock, CO (US); Orlando S Hoilett, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 171 days.

(21) Appl. No.: 17/073,223

(22) Filed: Oct. 16, 2020

(65) Prior Publication Data
US 2021/0161467 A1    Jun. 3, 2021

Related U.S. Application Data

(63) Continuation-in-part of application No. 17/035,018, filed on Sep. 28, 2020, which is a continuation of
(Continued)

(51) Int. Cl.
*A61B 5/00* (2006.01)
*A61B 5/11* (2006.01)
(Continued)

(52) U.S. Cl.
CPC ............ *A61B 5/681* (2013.01); *A61B 5/0205* (2013.01); *A61B 5/1112* (2013.01); *A61B 5/14552* (2013.01); *A61B 5/4833* (2013.01); *A61B 5/7207* (2013.01); *A61B 5/7257* (2013.01); *A61B 5/743* (2013.01); *A61B 5/0022* (2013.01); *A61B 5/02433* (2013.01); *A61B 5/0816* (2013.01); *A61B 2503/12* (2013.01);
(Continued)

(58) Field of Classification Search
CPC ... A61B 5/681; A61B 5/0205; A61B 5/14552; A61B 5/7257; A61B 5/743; A61B 5/0022; A61B 5/0816; A61B 2560/0214; A61B 2562/0219
See application file for complete search history.

(56) References Cited

U.S. PATENT DOCUMENTS 5,148,812 A * 9/1992 Verrier .................... A61B 5/35
600/517
5,810,722 A * 9/1998 Heikkila ................ A61B 5/222
600/300
(Continued)

OTHER PUBLICATIONS

Cretikos et al., Respiratory rate: the neglected vital sign, Med. J. Aust., vol. 188, No. 11, pp. 657-659, 2008.
(Continued)

*Primary Examiner* — Mallika D Fairchild
(74) *Attorney, Agent, or Firm* — Pirozzi-IP, LLC

(57) ABSTRACT

This invention generally relates to methods useful for measuring heart rate, respiration conditions, and oxygen saturation and a wearable device that incorporate those methods with a computerized system supporting data collection, analysis, readout and sharing. Particularly this present invention relates to a wearable device, such as a wristwatch or ring, for real time measuring heart rate, respiration conditions, and oxygen saturation.

10 Claims, 32 Drawing Sheets

Related U.S. Application Data application No. 16/159,007, filed on Oct. 12, 2018, now Pat. No. 10,786,201.

(60) Provisional application No. 62/916,987, filed on Oct. 18, 2019, provisional application No. 62/571,299, filed on Oct. 12, 2017.

(51) Int. Cl.
| | | |
|---|---|---|
| *A61B 5/1455* | (2006.01) | |
| *A61B 5/0205* | (2006.01) | |
| *A61B 5/024* | (2006.01) | |
| *A61B 5/08* | (2006.01) | |

(52) U.S. Cl.
CPC .......... *A61B 2560/0214* (2013.01); *A61B 2560/0228* (2013.01); *A61B 2562/0219* (2013.01)

(56) References Cited

U.S. PATENT DOCUMENTS

| | | | | |
|---|---|---|---|---|
| 2005/0209521 | A1* | 9/2005 | Kettunen | A61B 5/7278 600/508 |
| 2010/0056881 | A1* | 3/2010 | Libbus | A61B 5/318 600/382 |
| 2014/0187941 | A1* | 7/2014 | Shusterman | A61B 5/02007 600/480 |
| 2014/0275854 | A1* | 9/2014 | Venkatraman | A61B 5/1123 600/479 |
| 2016/0120434 | A1* | 5/2016 | Park | G16H 50/30 600/301 |

OTHER PUBLICATIONS

Nicolò et al., Respiratory Frequency during Exercise: The Neglected Physiological Measure, Front. Physiol., vol. 8, Dec. 2017.

Allen et al., Photoplethysmography and its application in clinical physiological measurement, Physiol. Meas., vol. 28, No. 3, p. R1, 2007.

Chon et al., Estimation of Respiratory Rate From Photoplethysmogram Data Using Time-Frequency Spectral Estimation, IEEE Trans. Biomed. Eng., vol. 56, No. 8, pp. 2054-2063, Aug. 2009.

Hoilett et al., Kick LL: A Smartwatch for Monitoring Respiration and Heart Rate using Photoplethysmography, in 2018 40th Annual International Conference of the IEEE Engineering in Medicine and Biology Society (EMBC), Honolulu, HI, 2018, pp. 3821-3824.

Hirsch et al., Respiratory sinus arrhythmia in humans: how breathing pattern modulates heart rate, Am. J. Physiol.-Heart Circ. Physiol., vol. 241, No. 4, pp. H620-H629, Oct. 1981.

Giardino et al., Respiratory sinus arrhythmia is associated with efficiency of pulmonary gas exchange in healthy humans. Am. J. Physiol -Heart Circ. Physiol., vol. 284, No. 5, pp. H1585-H1591, May 2003.

Yasuma et al., Respiratory Sinus Arrhythmia, Chest, vol. 125, No. 2, pp. 683-690, Feb. 2004.

Butler et al., Respiratory sinus arrhythmia, emotion, and emotion regulation during social interaction, Psychophysiology, vol. 43, No. 6, pp. 612-622, Nov. 2006.

Kim et al., Measurement Accuracy of Heart Rate and Respiratory Rate during Graded Exercise and Sustained Exercise in the Heat Using the Zephyr BioHarness™, Int. J. Sports Med., vol. 34, No. 6, pp. 497-501, Jun. 2013.

Müller et al., The Accuracy of Heart Rate Monitoring by Some Wrist-Worn Activity Trackers, Ann. Intern. Med., vol. 166, No. 8, pp. 610-612, Apr. 2017.

Cadmus-Bertram et al., The Accuracy of Heart Rate Monitoring by Some Wrist-Worn Activity Trackers, Ann. Intern. Med., vol. 166, No. 8, pp. 610-612, Apr. 2017.

Al-Khalidi et al., Respiration rate monitoring methods: A review, ediatric Pulmonology, vol. 46, No. 6, pp. 523-529, Jun. 2011.

Ben-Tal et al., Evaluating the physiological significance of respiratory sinus arrhythmia: looking beyond ventilation-perfusion efficiency: Respiratory sinus arrhythmia function, The Journal of Physiology, vol. 590, No. 8, pp. 1989-2008, Apr. 2012.

\* cited by examiner

METHOD OF MONITORING RESPIRATORY RATE IN A HEALTH MONITORING DEVICE

CROSS-REFERENCE TO RELATED APPLICATIONS

The present U.S. patent application is related to and claims the priority benefit of U.S. Provisional Patent Application Ser. No. 62/916,987, filed Oct. 18, 2019, and is a continuation-in-part patent application and claims the priority benefit of U.S. Non-Provisional patent application Ser. No. 17/035,018 filed Sep. 28, 2020, which is a continuation and claims the benefit of U.S. Non-Provisional patent application Ser. No. 16/159,007 filed Oct. 12, 2018, now U.S. Pat. No. 10,786,201 to Linnes et al., which claims the priority benefit of U.S. Provisional Patent Application Ser. No. 62/571,299, filed Oct. 12, 2017, the contents of each of which is hereby incorporated by reference in its entirety into the present disclosure.

GOVERNMENT SUPPORT CLAUSE

This invention was made with government support under grant DA038886, awarded by the National Institutes of Health. The government has certain rights in the invention.

TECHNICAL FIELD

This invention generally relates to a method useful for measuring heart rate, respiration conditions, and oxygen saturation and a wearable device that incorporate said method with a computerized system supporting data collection, analysis, readout and sharing.

BACKGROUNDS AND SUMMARY OF THE INVENTION

This section introduces aspects that may help facilitate a better understanding of the disclosure. Accordingly, these statements are to be read in this light and are not to be understood as admissions about what is or is not prior art.

Wearable devices are getting more popularity almost on daily basis, rapidly advancing in terms of technology, functionality, and size, with more real-time applications. A wearable device, wearable technology, or a wearable gadget is a category of technology devices that can be worn by a consumer and often include tracking information related to health and fitness. A wearable device as disclosed herein refers to a wristwatch, a ring or a necklace. Any additional capabilities to those device will add more value and enhance their popularity, not only to everyday people on the street, but also to those sick and feeble in need of special cares. Additionally, a wearable device may also find uses in remote monitoring and diagnosis of patients' health conditions.

Photoplethysmography (PPG) is a simple, optical technique used to detect volumetric changes in blood in peripheral circulation. It is a low-cost and non-invasive method that makes measurements at the surface of the skin. PPG makes uses of low intensity infrared (IR) light. When light travels through biological tissues, it is absorbed by bones, skin pigments as well as venous and arterial blood. Since light is more strongly absorbed by blood than other surrounding tissues, the volumetric changes in blood flow can be detected by PPG sensors as changes in the intensity of light. The voltage signal from PPG is proportional to the quantity of blood flowing through the blood vessels. Blood flow variations mostly occur in the arteries, and not much in the veins. Other factors affecting the recordings from the PPG are the site of measurement, the contact force between the site and the sensor, as well as the skin color at the site of measurement.

The measurements provide valuable information related to the cardiovascular system and are widely used in clinical physiological measurements and monitoring, including heart rate and pulse oximetry. Existing PPG technologies apply sensors to the finger, but this technique suffer from lack of mobility. Numerous technologies can be worn on the wrist; however, they are unable to detect respiration or blood oxygenation levels. There is need of more practical method for monitoring health via PPG that can detect all needed measurements.

This invention generally relates to a method useful for measuring heart rate, respiration conditions, and oxygen saturation and a wearable device that incorporate those methods with a computerized system supporting data collection, analysis, readout and sharing. Particularly this present invention relates to a wearable device, such as a wristwatch, for real time measuring heart rate, respiration conditions, and oxygen saturation, wherein those data can be shared and distributed remotely.

BRIEF DESCRIPTION OF THE DRAWINGS

Embodiments of the present disclosure will now be described by way of example in greater detail with reference to the attached figures, in which.

Additionally, there is a few seconds delay between each snapshot resulting in the difference in HR and RR reported by the reference device (viewed on the smartphone), which has a faster refresh rate than the experimental device.

Figure 5A:
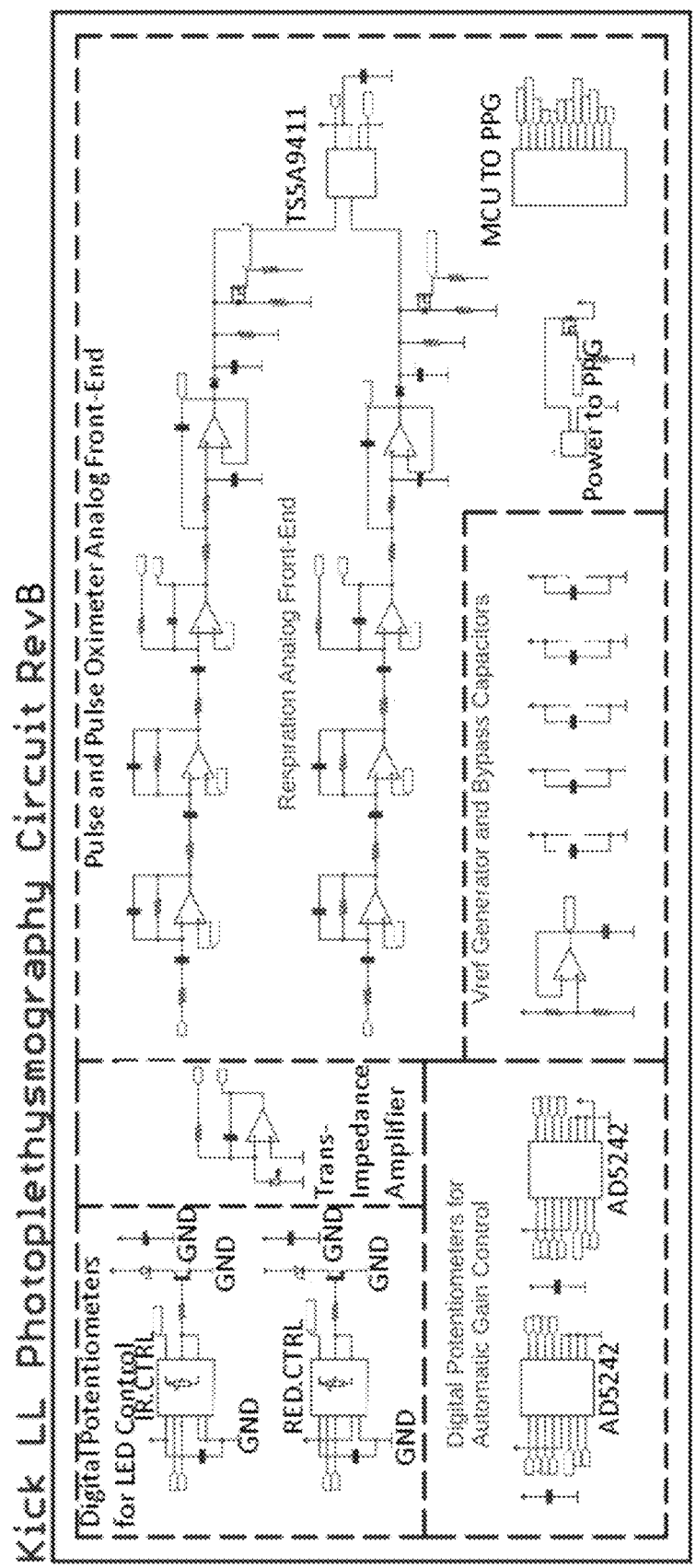

FIG. 5A shows our schematic for our biometric sensor board. In this design, we depict our amplification and filtering scheme for measuring heart rate, respiration, and pulse oximetry. We have a dual LED (red and infrared) in which we are able to automatically control the brightness of the LEDs to account for difference in skin tones.

Figure 5B:
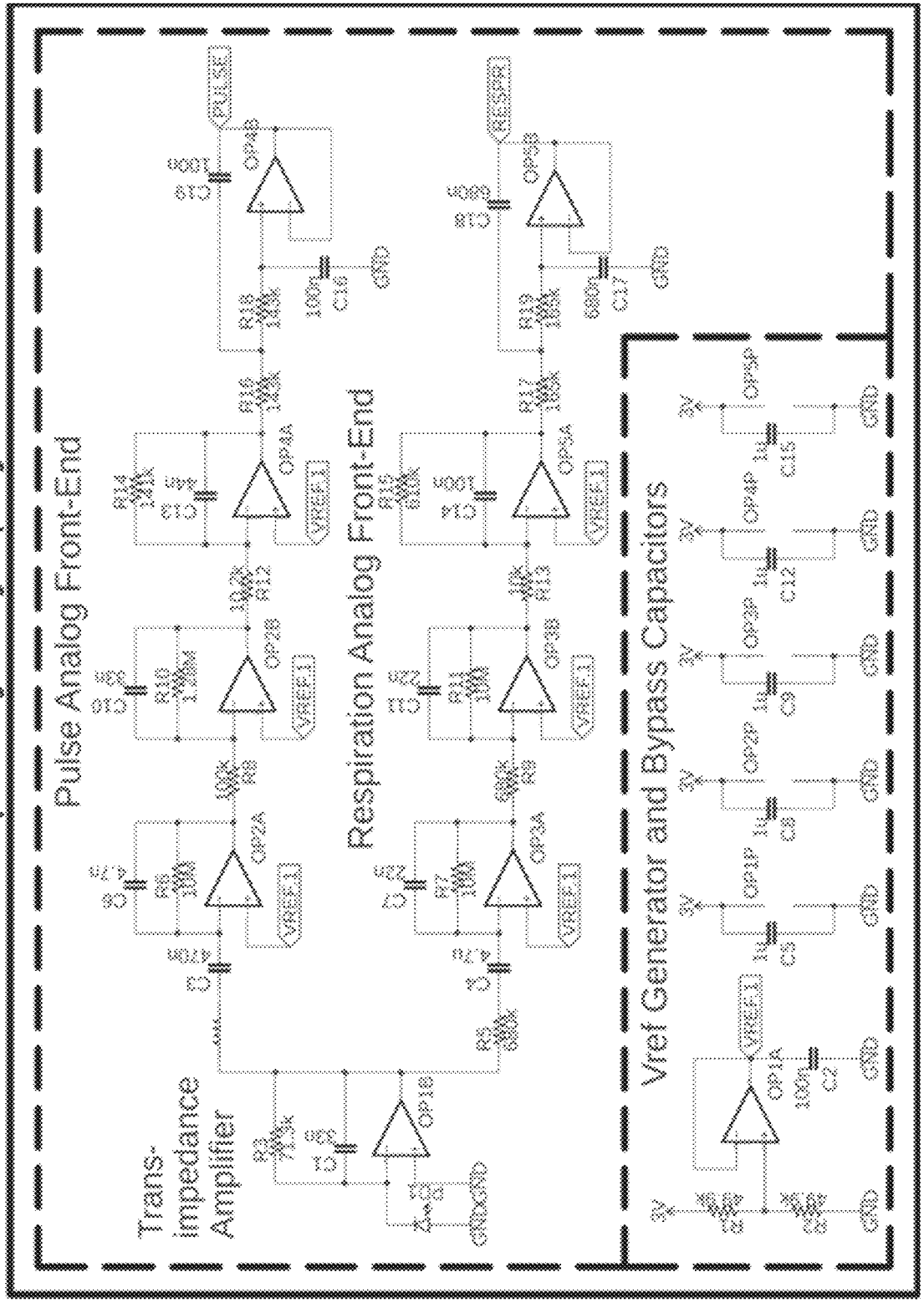

FIG. 5B shows schematic of the photoplethysmography (PPG) sensing circuit. The signal from the transimpedance amplifier is sent into two sets of cascaded active filters tuned for heart rate sensing and respiration monitoring, respectively. The outputs of the amplifier stages are sensed by two channels of an on-board 10-bit analog-to-digital converter on a Bluetooth-enabled microcontroller. The signals are processed by the on-board microcontroller. R3, R14, and R15 (highlighted with a dashed box) are digitally controlled potentiometers enabling automatic gain control. Using these potentiometers, the microcontroller can modulate system gain in order to adjust for differences in the optical reflective properties of skin across difference subjects.

Figure 6:
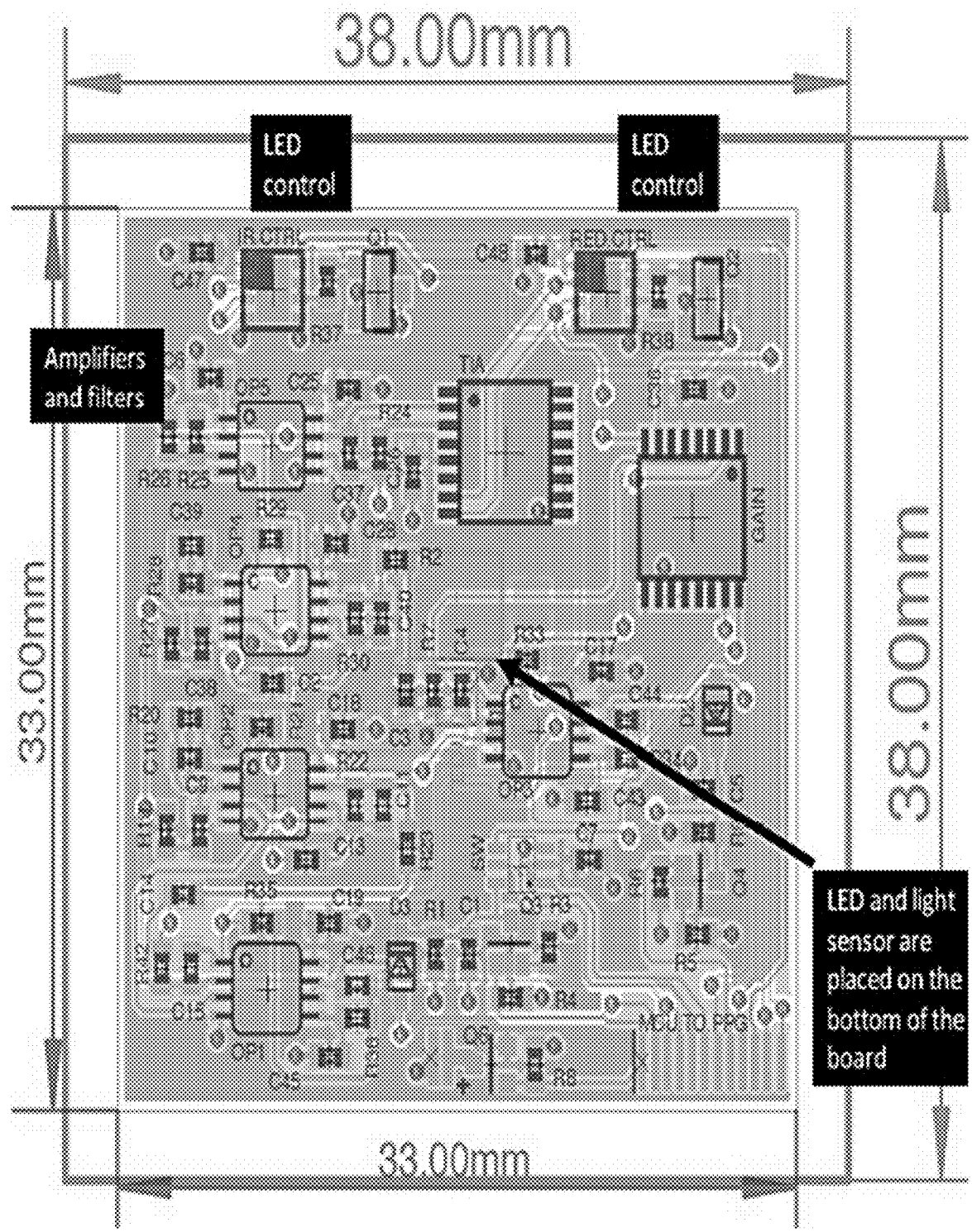

FIG. 6 depicts the circuit board design for our biometric sensor board showing how the circuit board is physically laid out in space. Along the left side are the amplifiers and filters. At the center and bottom of the board are the LEDs and light sensor. At the top is the brightness control mechanism for the LEDs.

Figure 7:
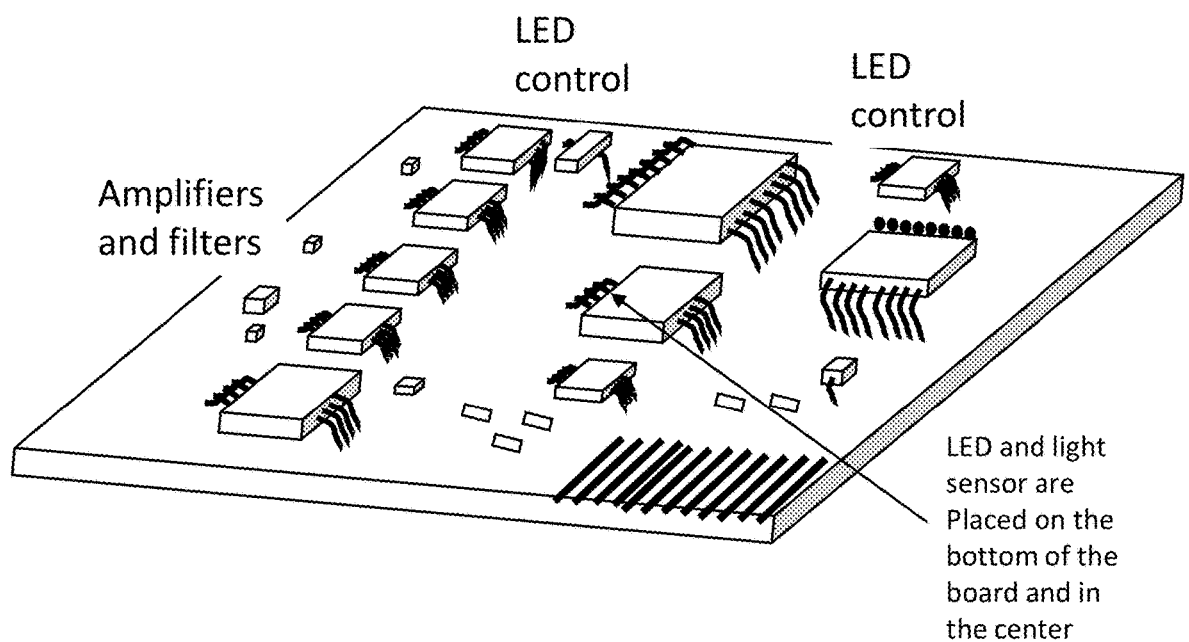

FIG. 7 shows the back side of the circuit board.

Figure 8:
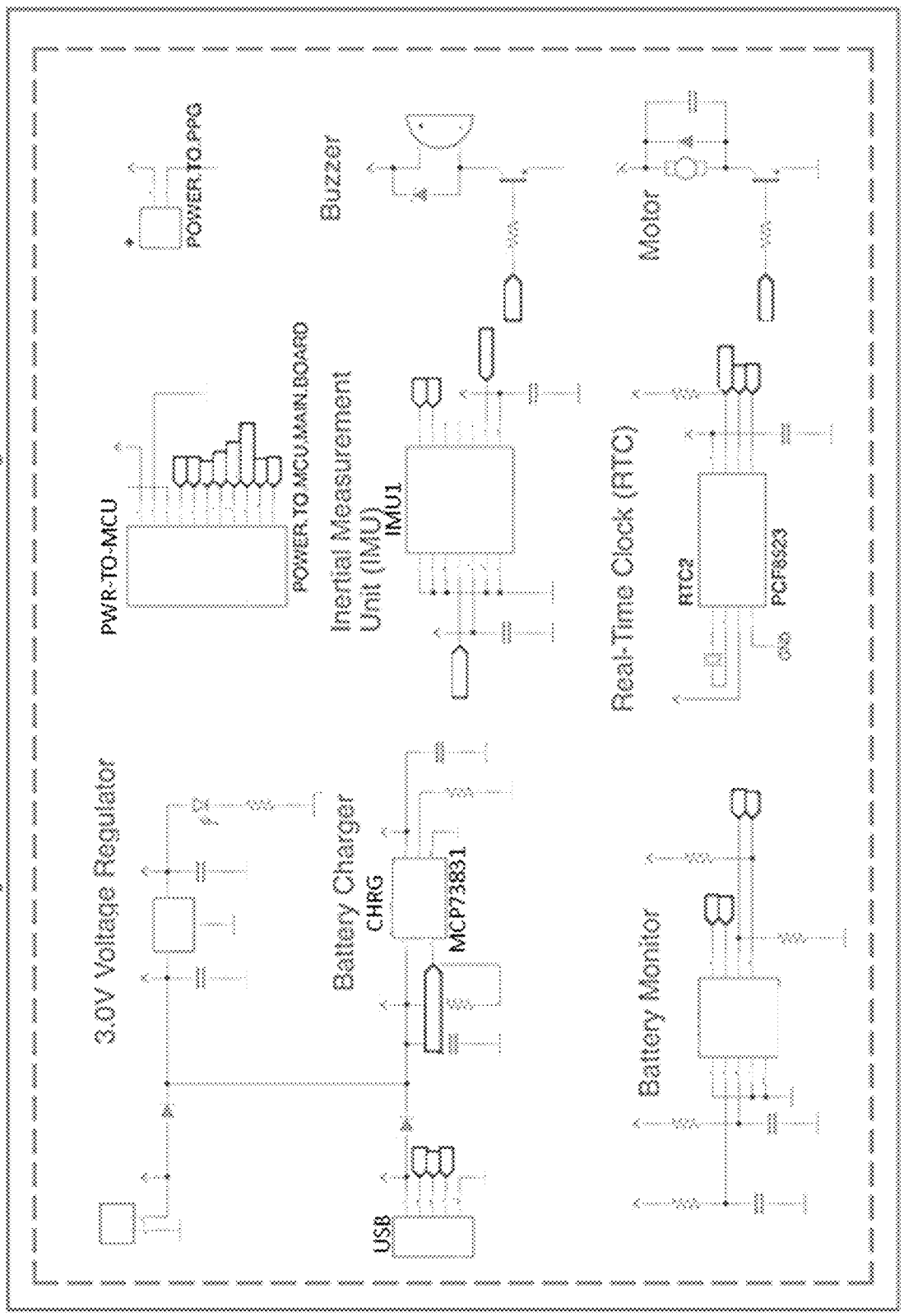

FIG. 8 shows This slide shows our auxiliary sensor board that contains battery management systems (voltage regulation, battery charging, battery status), a locomotion sensor (accelerometer and gyroscope), a real-time clock (for accurate time keeping), a motor (for user feedback), and a buzzer (also for user tactile feedback).

Figure 9:
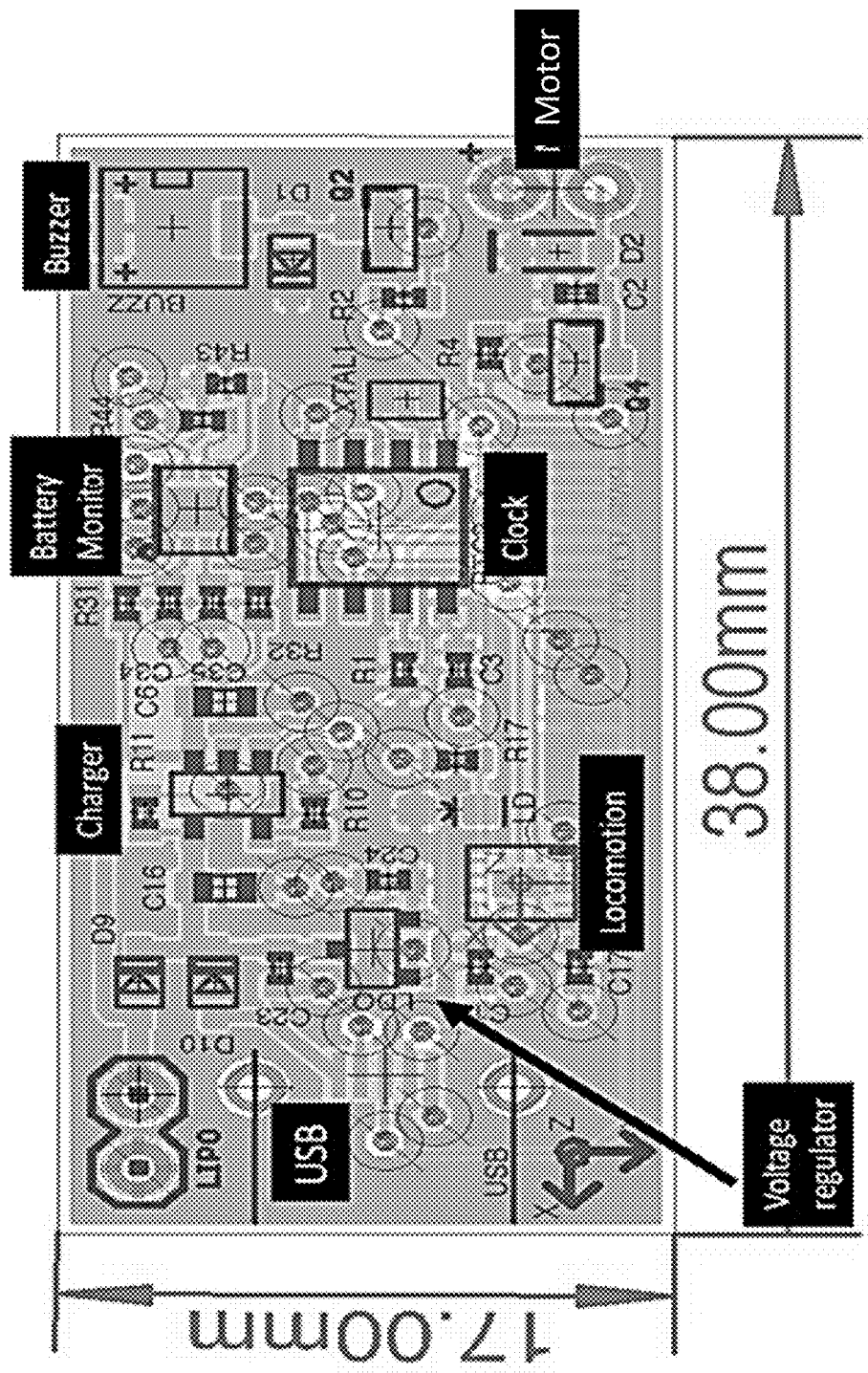

FIG. 9 shows the circuit board layout for the auxiliary sensor board and where all the components are laid out.

Figure 10:
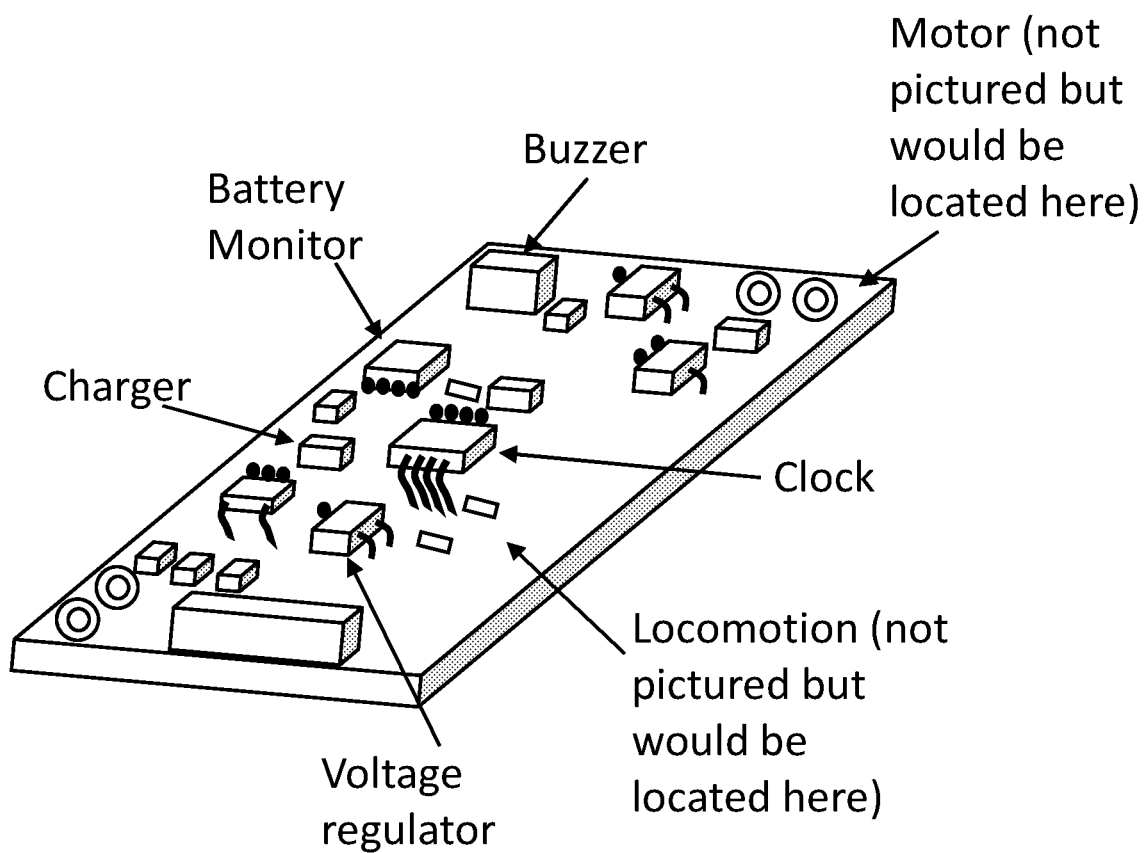

FIG. 10 shows the communications and central processing board that contains our Bluetooth capable central processing unit, an external memory chip (RAM), a screen for displaying information to the user (OLED), an SD card for long term data storage, and buttons for user input. This board handles all the data processing to measure heart rate, respiratory rate, and pulse oximetry. This board is also responsible for controlling all other boards and for sending data to the user.

Figure 11A:
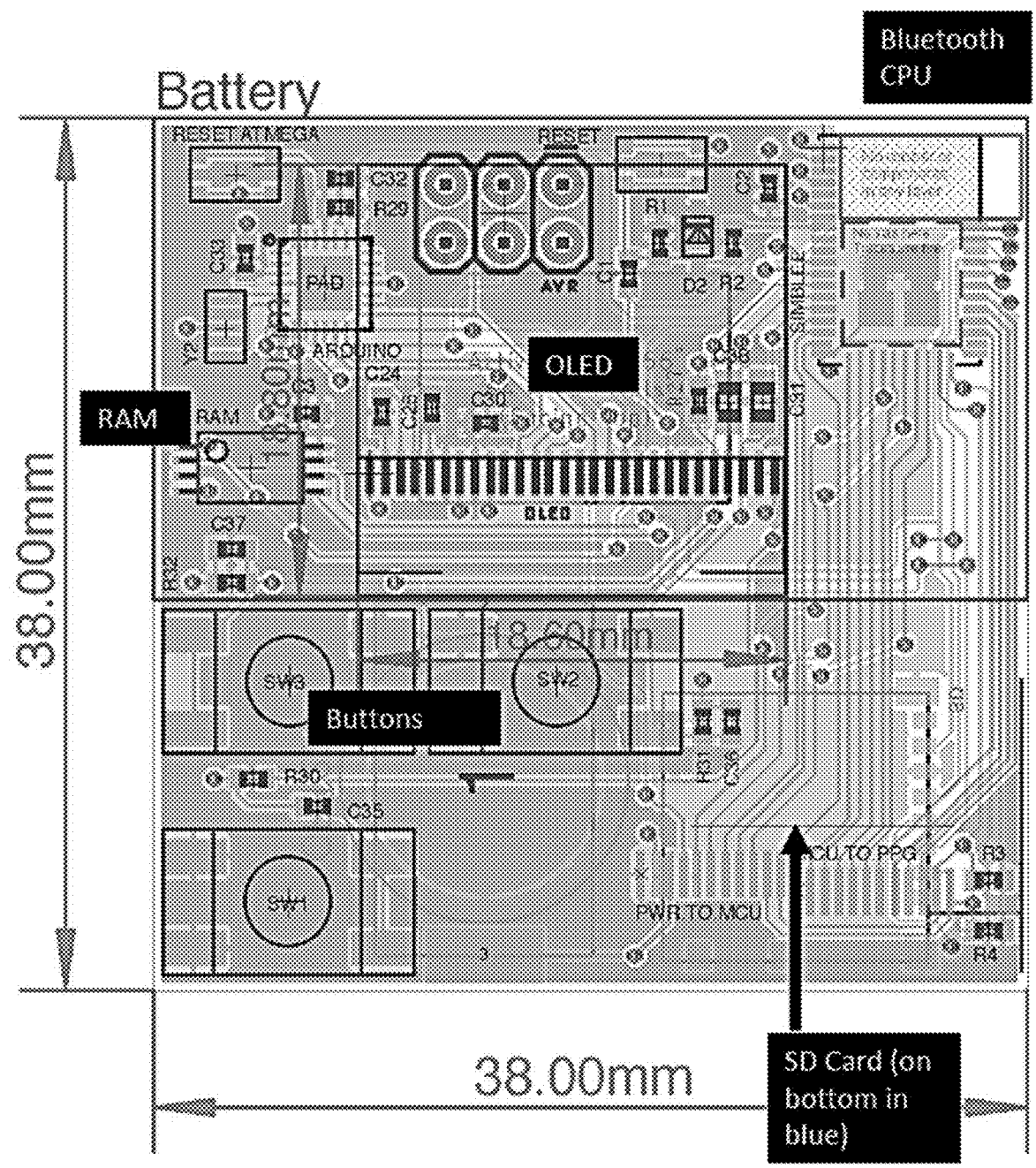

FIG. 11A depicts the circuit board layout for our communications and central processing board.

Figure 11B:
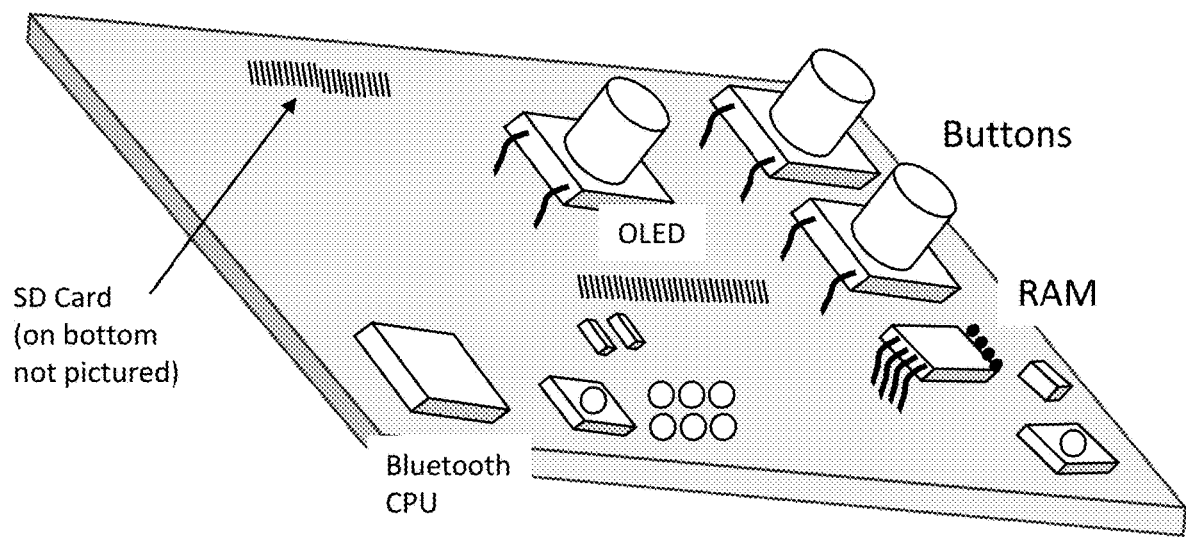

FIG. 11B shows the back side of the circuit board

Figure 12:
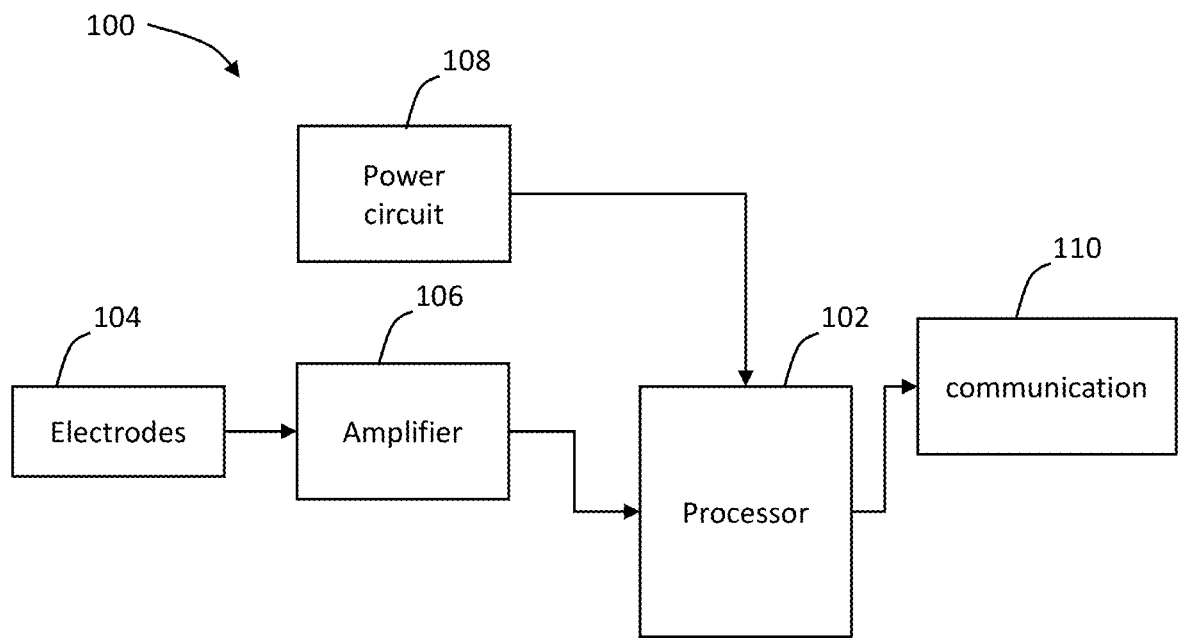

FIG. 12 is a block diagram of an alternate heart rate and respiration system according to the present disclosure.

Figure 13:
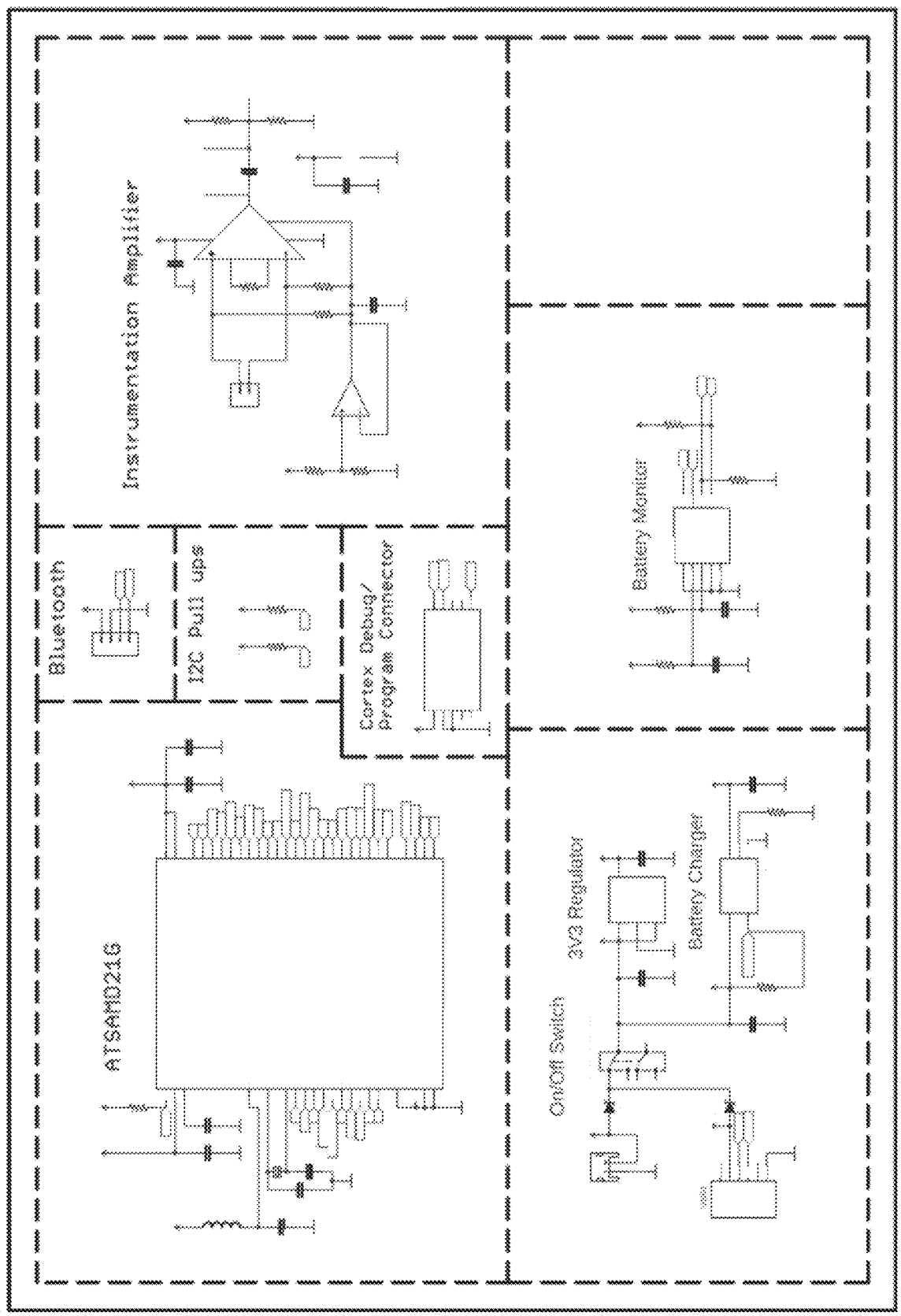

FIG. 13 is a circuit of the system shown in FIG. 12.

Figure 14:
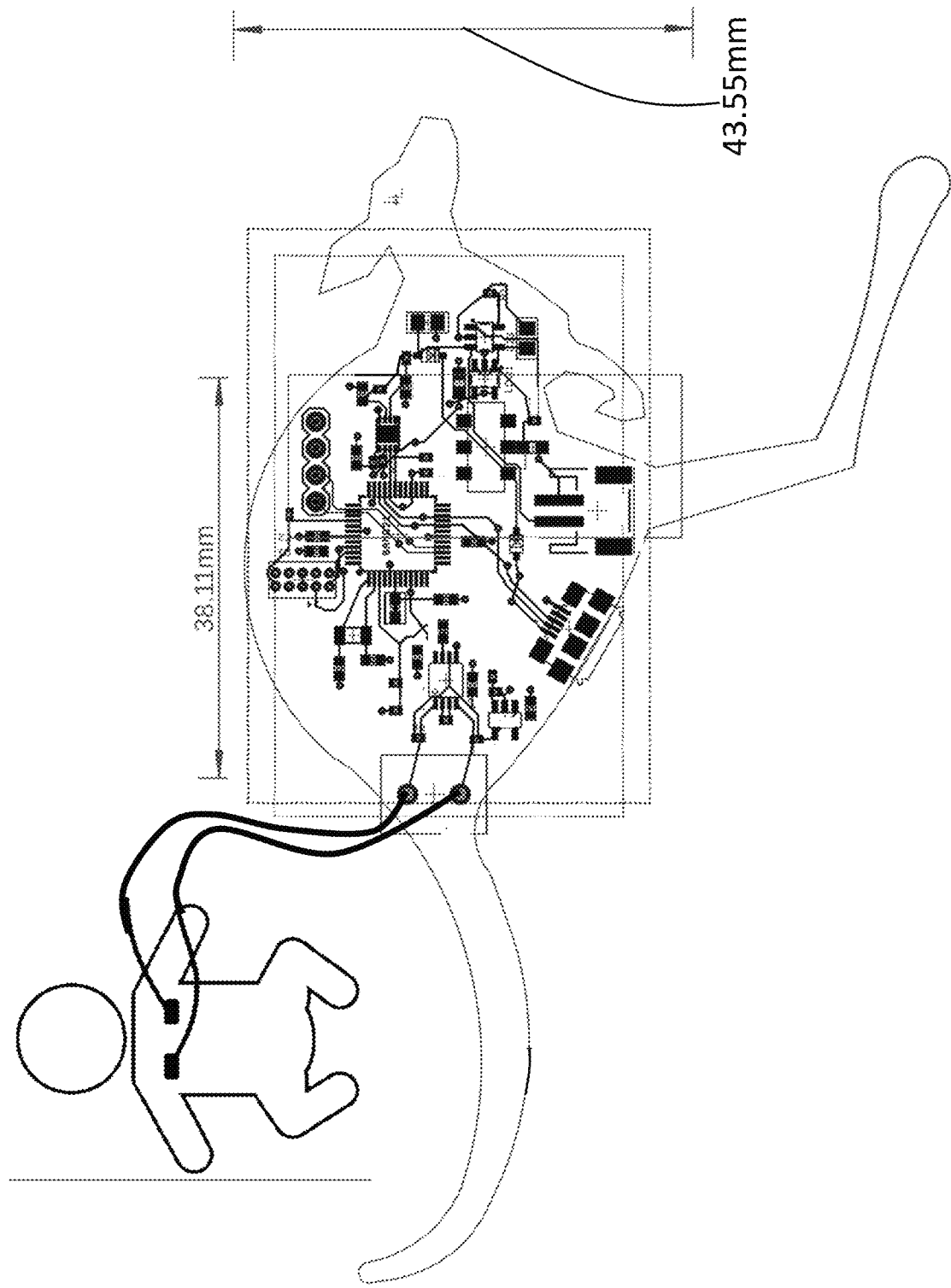

FIG. 14 is a schematic of a layout of the system of FIG. 12 with actual dimensions.

Figure 15:
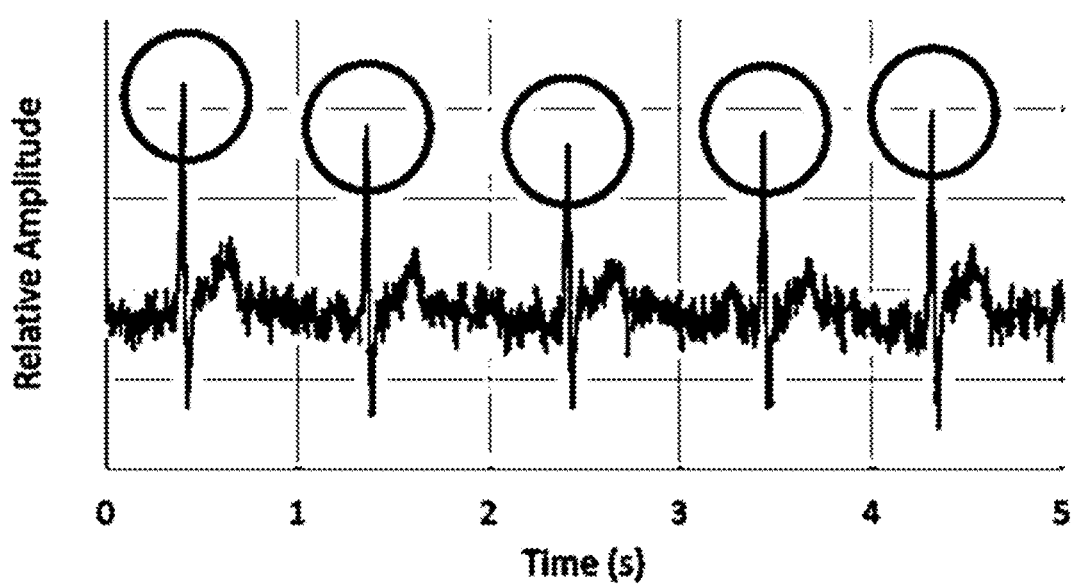

FIG. 15 is a plot of relative amplitude vs. time in seconds of the PQRST waves with the peaks of the R-waves marked with circles.

Figure 16:
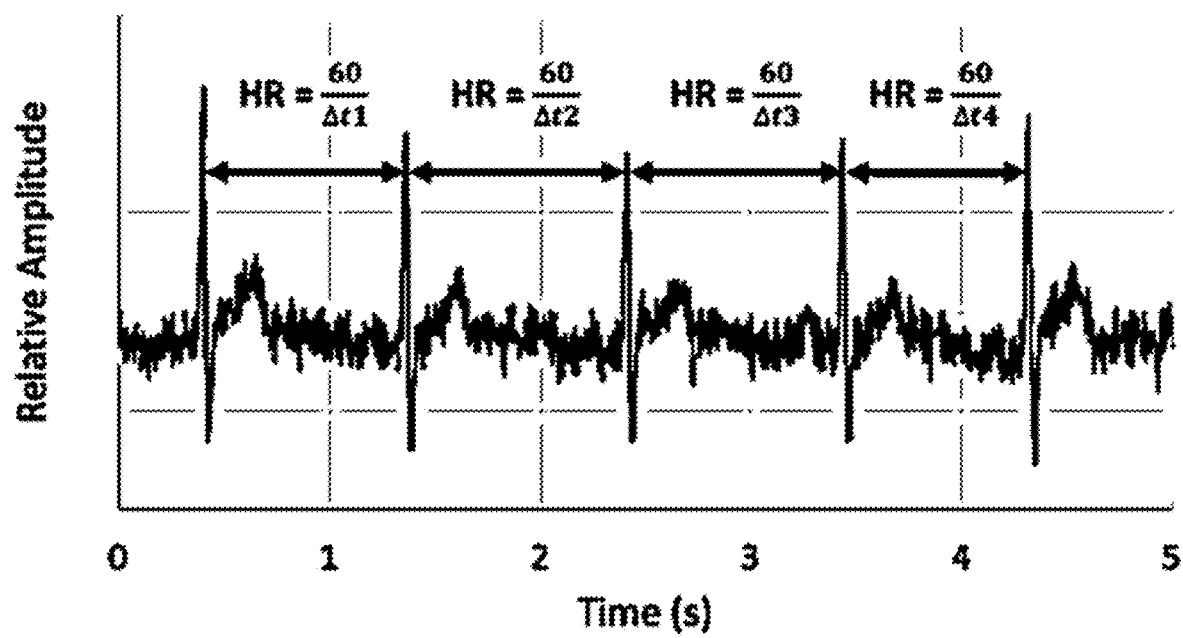

FIG. 16 is a graph of relative amplitude vs. time in seconds with intra-timing between R-wave peaks shown as $\Delta t1$, $\Delta t2$, $\Delta t3$, $\Delta t4$, and so on with heart rate (HR) calculated based on dividing 60 by each intra-timing between R-wave peaks (i.e., $HR1=60/\Delta t1$, $HR2=60/\Delta t2$, $HR3=60/\Delta t3$, $HR4=60/\Delta t4$, and so on).

Figure 17:
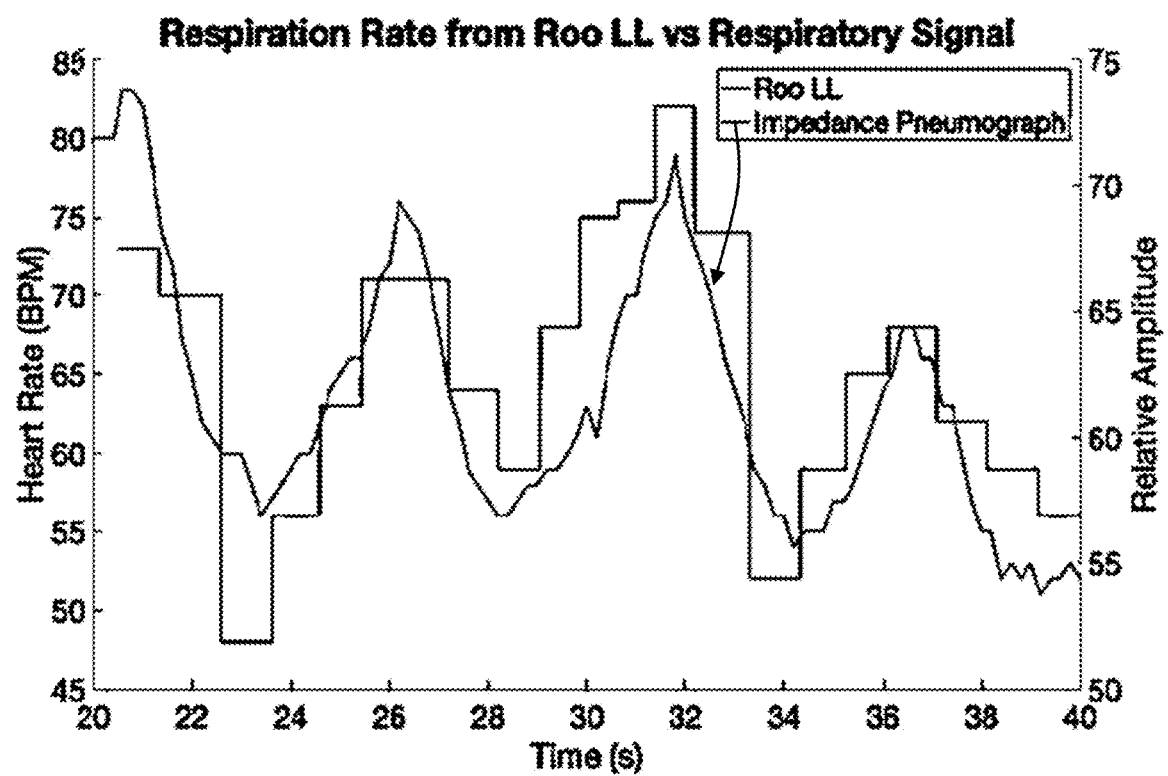
Figure 18:
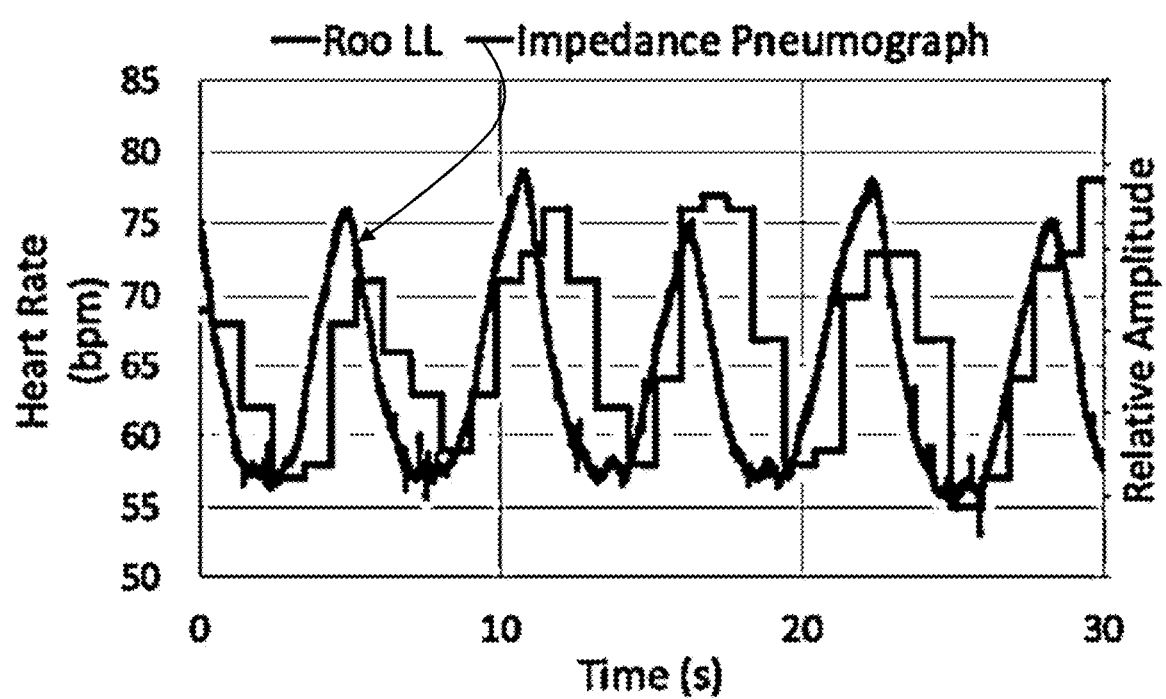

FIGS. 17 and 18 are complex graphs of heart rate in beats per minute (BPM) and relative amplitude vs. time in seconds, and which can be translated to instantaneous respiratory rate by measuring the time between the heart rate local maximums.

Figure 19:
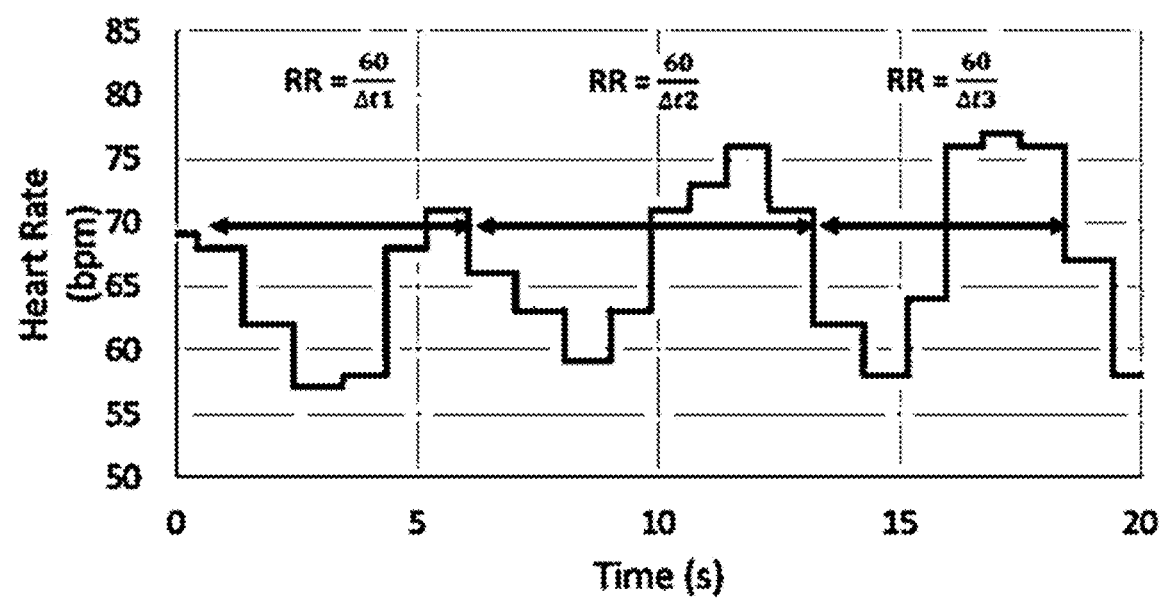

FIG. 19 is a graph of heart rate in BMP vs. time in seconds and which shows instantaneous heart rate calculated over time.

Figure 20:
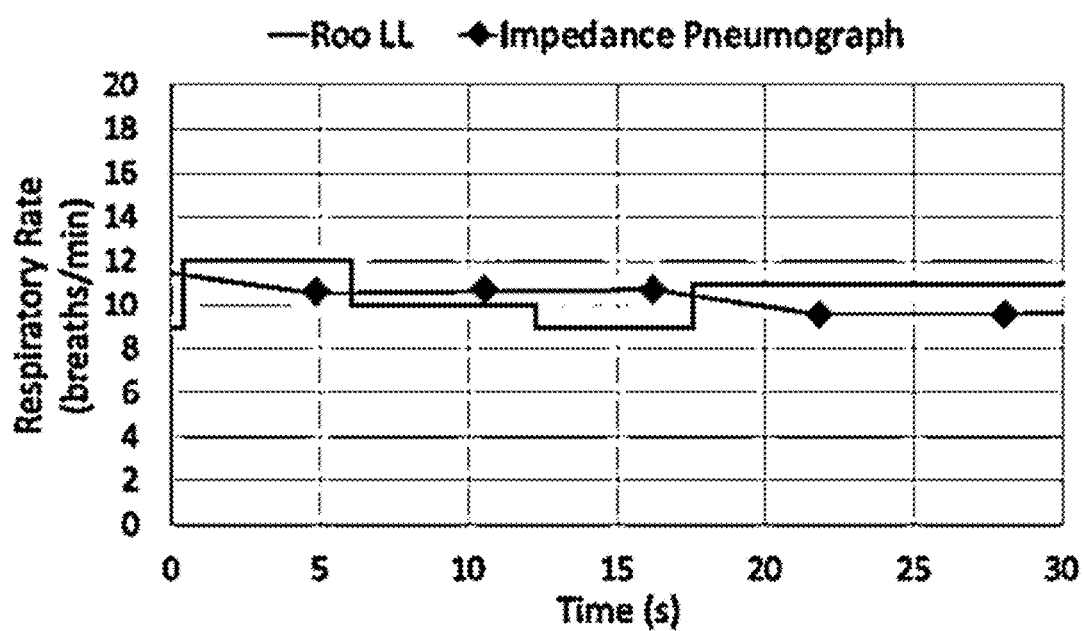

FIG. 20 is another graph of respiratory rate (i.e., breaths per minute) vs. time in seconds comparing the results of the system of the present disclosure vs. the gold standard (impedance pneumography).

Figure 21:
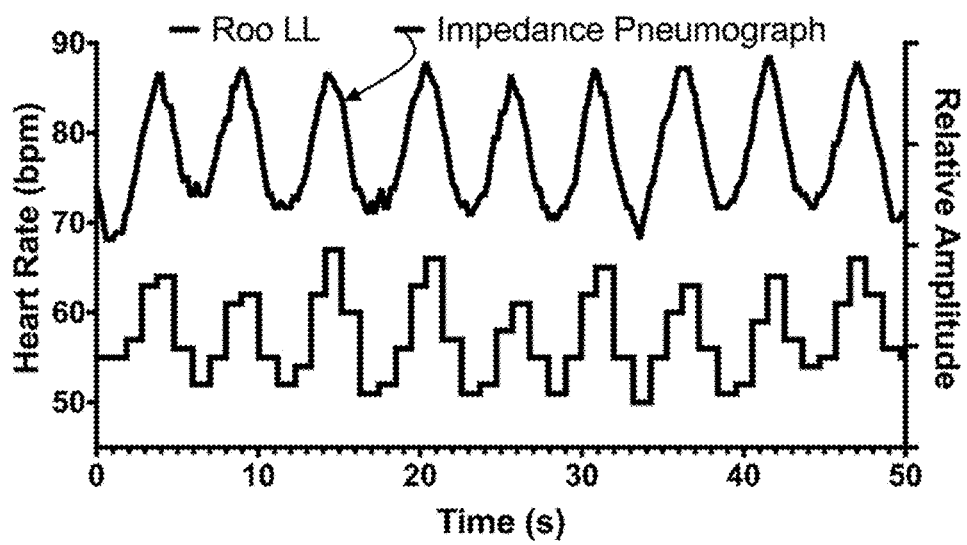

FIG. 21 are graphs of heat rate in BPM vs. time (FIG. 21) the calculated respiratory rate, i.e., breaths per minute vs. time in seconds (FIG. 22), both shown with comparison to the gold standard of impedance pneumography, outputs of the system of the present disclosure are shown during breath hold periods with excellent correlation against the gold standard.

Figure 23:
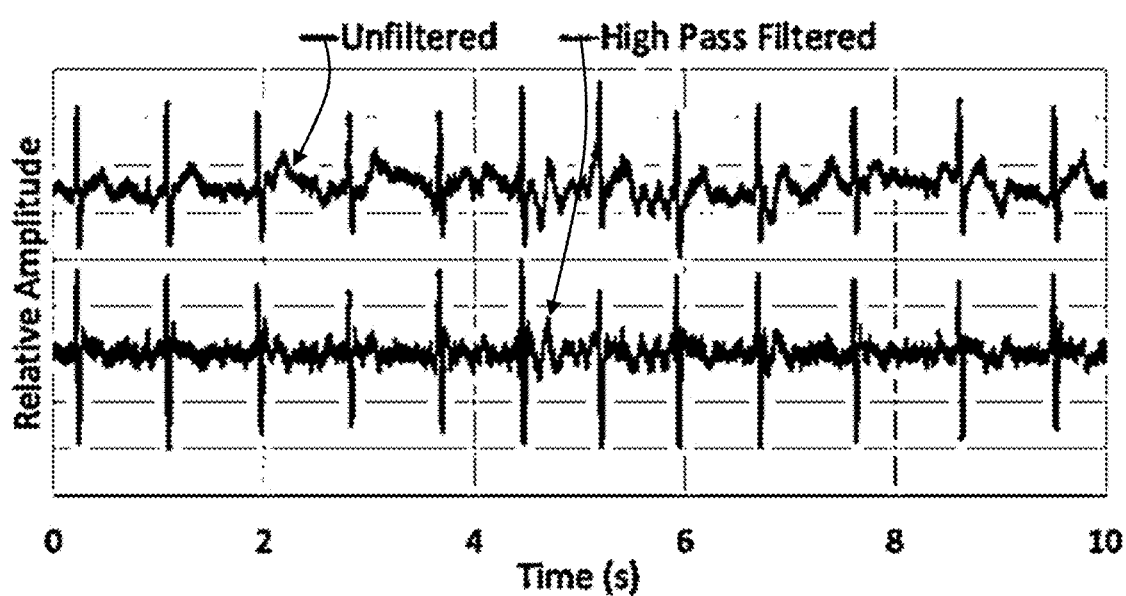

FIG. 23 are two graphs of relative amplitude vs. time in seconds of the PQRST waveform with one shown as an unfiltered signal and the other as a high-pass filtered signal.

Figure 24:
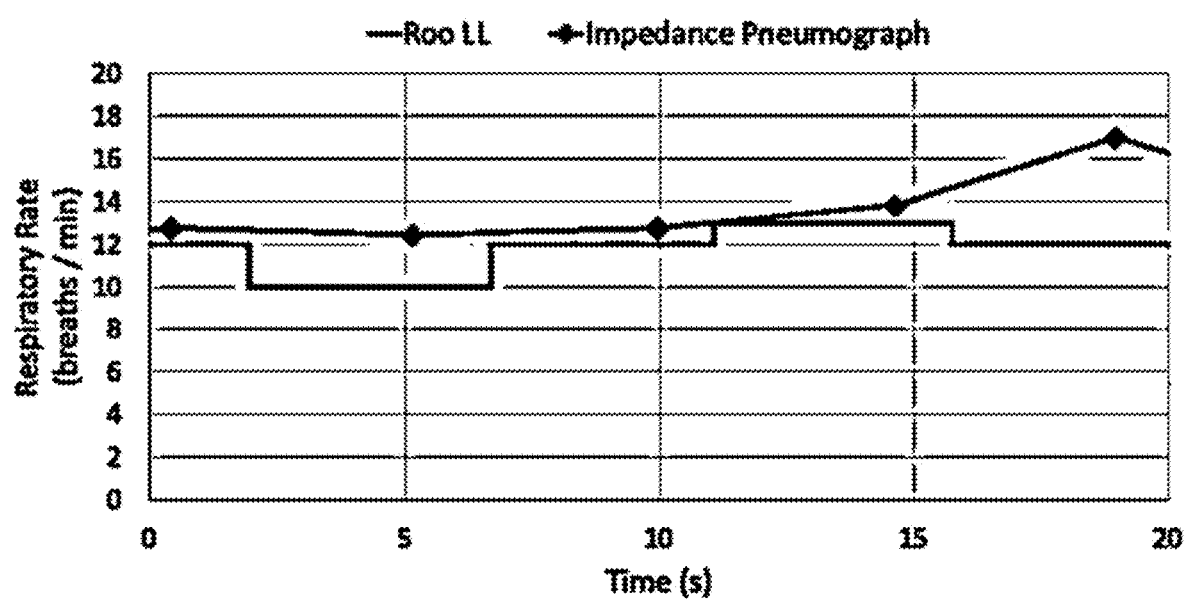

FIG. 24 is a graph showing a comparison with gold standard for respiratory rate in breaths per minute vs. time in seconds over a period of time when the subject is moving.

Figure 25:
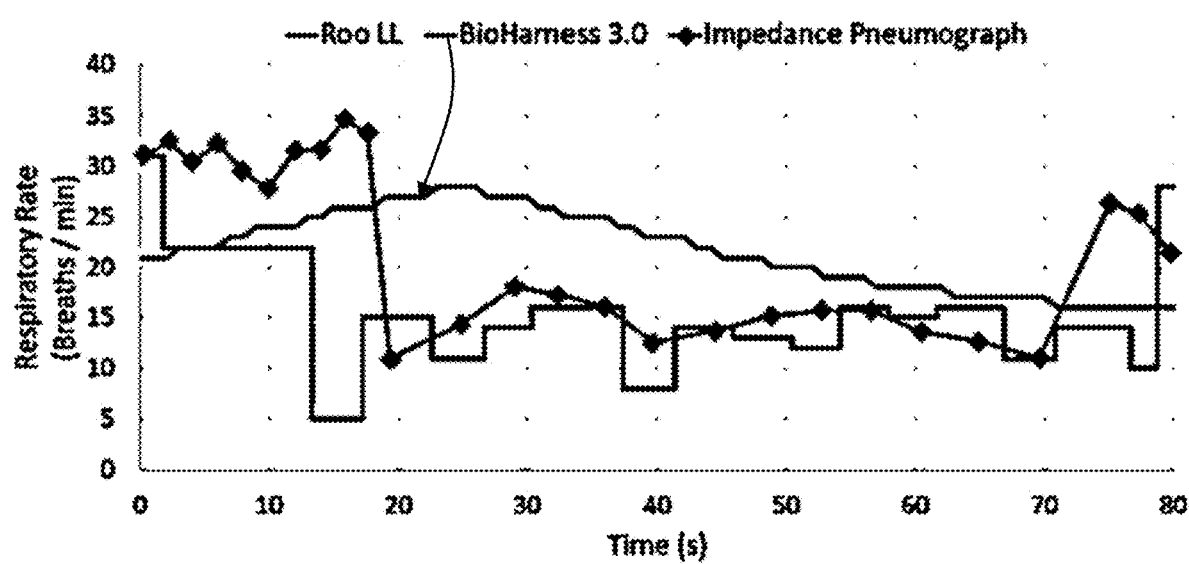

FIG. 25 is a graph of respiratory rate in breaths per minute vs. time in seconds for three approaches including the system of the present disclosure, a commercial device, and the gold standard with excellent correlation.

Figure 26:
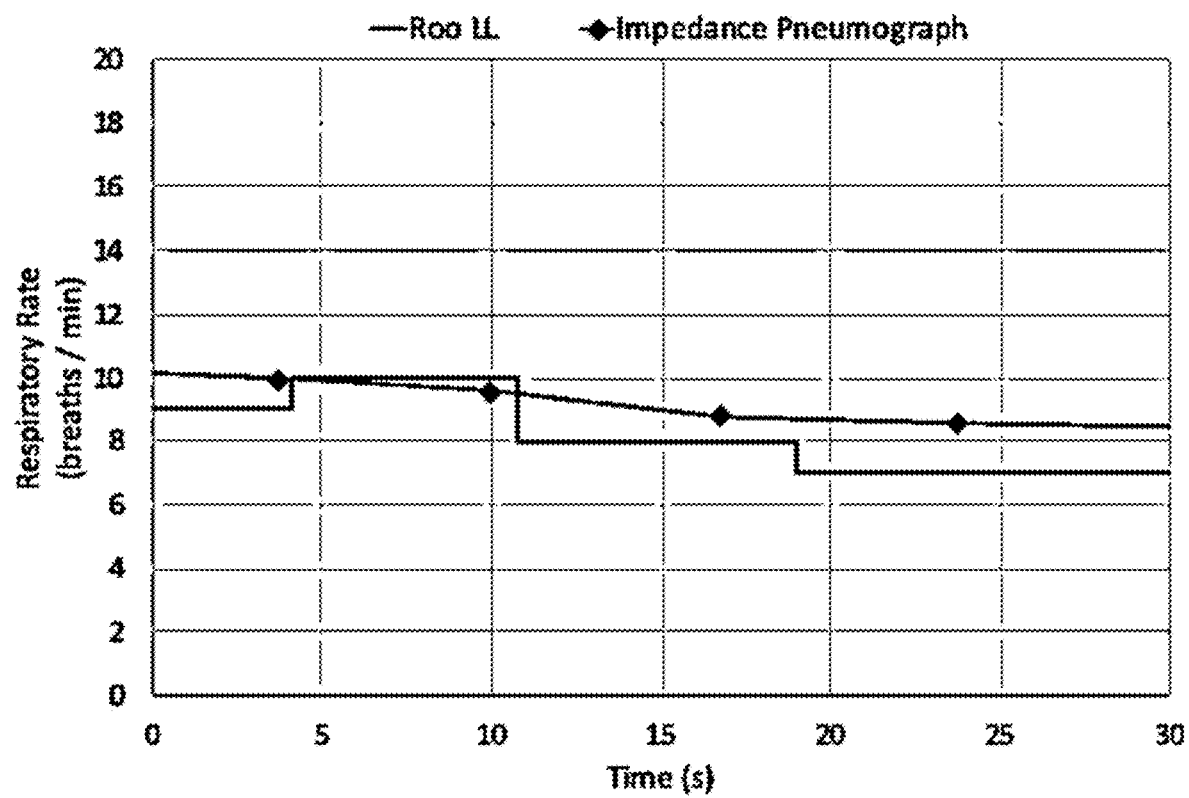

FIG. 26 is a graph of respiratory rate in breaths per minute vs. time in seconds with electrodes placed on the back of the subject.

Figure 27:
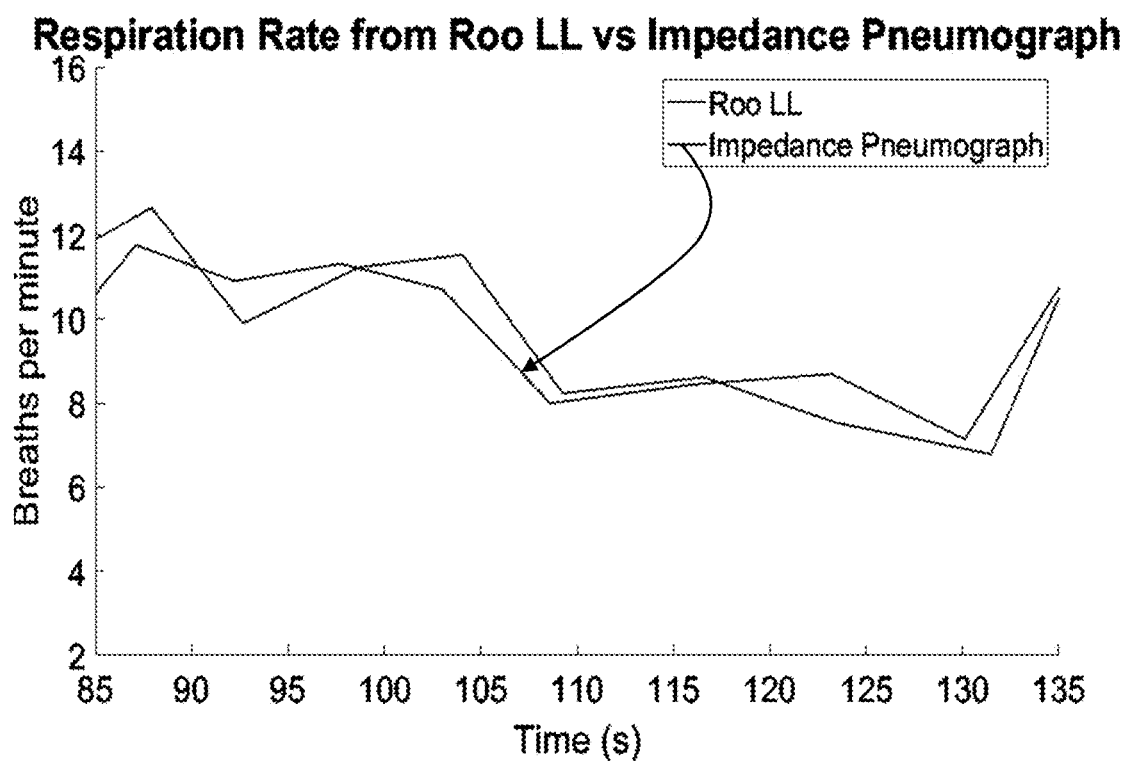
Figure 28:
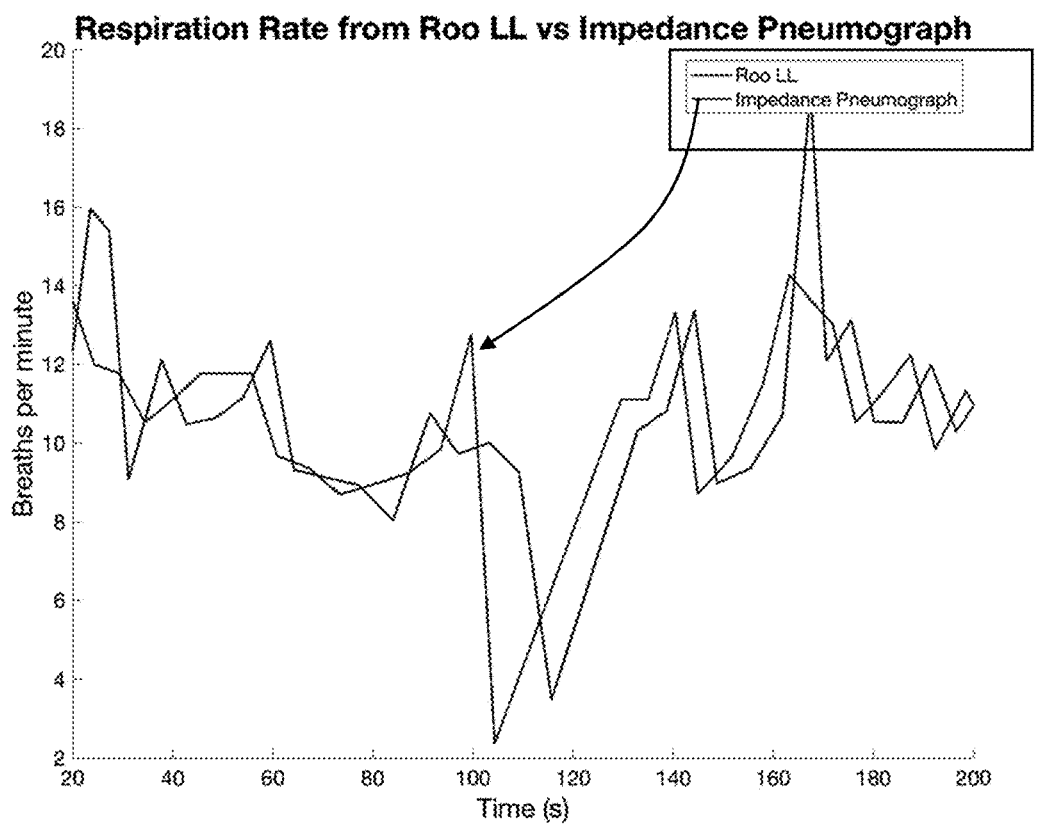

FIGS. 27 and 28 are graphs of comparisons of breaths per minute vs. time in seconds based on the output of the system of the present disclosure and as compared to the gold standard for when the subject is walking (FIG. 27) and during breath holds (FIG. 28), again showing excellent tracking as compared to the gold standard of impedance pneumography.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

This invention generally relates to a method useful for measuring heart rate, respiration conditions, and oxygen saturation and a wearable device that incorporate those methods with a computerized system supporting data collection, analysis, and readout. Particularly this present invention relates to a wearable device, such as a wristwatch, a ring or a necklace, for real time measuring heart rate, respiration conditions, and oxygen saturation.

In some illustrative embodiments, the invention relates to a method for measuring heart rate, respiration, and oxygen saturation of a subject comprising extracting and processing photoplethysmographic (PPG) data from said subject and displaying a readout on a wearable device.

In some illustrative embodiments, the invention relates to a method for measuring heart rate, respiration, and oxygen saturation of a subject with a single device comprising the step of
  a) measuring reflectance of red and infrared lights off skin tissue using a biometric sensor board;
  b) processing and analyzing data collected in step a); and
  c) displaying and/or sharing results of the processed data remotely.

In some illustrative embodiments, the invention relates to a method for measuring heart rate, respiration, and oxygen saturation of a subject with a single device as disclosed herein, wherein the subject is a human patient or a healthy subject in need of monitoring for safety purpose.

In some illustrative embodiments, the invention relates to a method for measuring heart rate, respiration, and oxygen saturation of a subject with a single device as disclosed herein, wherein said device is a wearable device comprising a watch, a ring or a necklace.

In some illustrative embodiments, the invention relates to a method for measuring heart rate, respiration, and oxygen saturation of a subject with a single device as disclosed herein, wherein said biometric sensor board extracts and collects photoplethysmographic data from said subject.

In some illustrative embodiments, the invention relates to a method for measuring heart rate, respiration, and oxygen saturation of a subject with a single device as disclosed herein, wherein said biometric sensor board comprises a light sensor, a dual wavelength light source (red and infrared) with an auto-gain feedback loop for calibrating skin tones and pulse strength, and a plurality of active filters for an enhanced signal to noise ratio with an auto-gain feedback loop to maintain a reasonable signal strength for ease of signal processing.

In some illustrative embodiments, the invention relates to a method for measuring heart rate, respiration, and oxygen saturation of a subject with a single device as disclosed herein, wherein said data processing and analyzing carried out by a microcontroller equipped with a central processing unit comprises noises elimination from extracted photoplethysmographic data using a motion tracking sensor for an enhanced signal to noise ratio.

In some illustrative embodiments, the invention relates to a method for measuring heart rate, respiration, and oxygen saturation of a subject with a single device as disclosed herein, wherein said motion tracking sensor is an accelerometer, a gyroscope, or a combination thereof.

In some illustrative embodiments, the invention relates to a method for measuring heart rate, respiration, and oxygen saturation of a subject with a single device as disclosed herein, wherein said data processing and analyzing comprises a frequency analysis using a Fourier Transform on data collected over several seconds of time, wherein said frequency is reasonably related to a biometric measurement of heart rate and respiration.

In some illustrative embodiments, the invention relates to a method for measuring heart rate, respiration, and oxygen saturation of a subject with a single device as disclosed herein, wherein said reasonable frequency for heart rate measurement ranges from about 0.4 Hertz (Hz) to about 4 Hz; said reasonable frequency for respiration measurement ranges from about 0.05 Hz to about 1.2 Hz; and said heart rate and respiration are determined by comparing the magnitude of a peak of the Fourier Transform for heart rate or respiration at each frequency to the magnitude of a peak in the Fourier Transform of the accelerometer/gyroscope data in all three axes at each frequency, respectively.

In some illustrative embodiments, the invention relates to a method for measuring heart rate, respiration, and oxygen saturation of a subject with a single device as disclosed herein, wherein said oxygen saturation in blood of said subject is determined by comparing the relative signal strength of red and infrared light collected over several seconds of time.

In some illustrative embodiments, the invention relates to a wearable device measuring heart rate, respiration and oxygen saturation of a subject can be displayed and/or shared remotely.

In some illustrative embodiments, the invention relates to a wearable device measuring heart rate, respiration and oxygen saturation of a subject can be displayed and/or shared remotely as disclosed herein, which further comprising a means for pinpointing the exact location of said subject for monitoring and detecting drug use or abuse of said subject remotely.

In some illustrative embodiments, the invention relates to a wearable device for measuring heart rate, respiration, and oxygen saturation of a subject comprising
  a) a biometric sensor board measuring reflectance of red and infrared lights off skin tissue;
  b) a microcontroller processing data collected by said photosensor, wherein a dedicated memory chip is installed for storing large amounts of data for real-time signal processing;
  c) a power supply; and
  d) a means for displaying and/or sharing results of the processed data.

In some illustrative embodiments, the invention relates to a wearable device for measuring heart rate, respiration, and oxygen saturation of a subject in a single device further comprising a motion tracking sensor for an enhanced signal to noise ratio by eliminating noises from extracted photoplethysmographic data.

In some illustrative embodiments, the invention relates to a wearable device for measuring heart rate, respiration, and oxygen saturation of a subject in a single device further comprising a motion tracking sensor for an enhanced signal to noise ratio by eliminating noises from extracted photoplethysmographic data, wherein said motion tracking sensor is an accelerometer, a gyroscope or a combination thereof.

In some illustrative embodiments, the invention relates to a wearable device for measuring heart rate, respiration, and oxygen saturation of a subject in a single device further comprising a real-time clock for accurate time keeping and a means for battery level monitoring.

In some illustrative embodiments, the invention relates to a wearable device for measuring heart rate, respiration, and oxygen saturation of a subject in a single device further comprising a means for pinpointing the location of said subject for monitoring and detecting drug use or abuse of said subject.

In some illustrative embodiments, the invention relates to a wearable device for measuring heart rate, respiration, and oxygen saturation of a subject in a single device further comprising input and output capabilities for charging, programming, and data transfer and sharing.

In some illustrative embodiments, the invention relates to a wearable device for measuring heart rate, respiration, and oxygen saturation of a subject in a single device further comprising means for long term and short term data storage.

In some illustrative embodiments, the invention relates to a wearable device for measuring heart rate, respiration, and oxygen saturation of a subject in a single device, wherein said biometric sensor board comprises a light sensor, a dual wavelength light source (red and infrared) with an auto-gain feedback loop for calibrating skin tones and pulse strength, and a plurality of active filters for an enhanced signal to noise ratio with an auto-gain feedback loop to maintain a reasonable signal strength for ease of signal processing.

In some illustrative embodiments, the invention relates to a wearable device for measuring heart rate, respiration, and oxygen saturation of a subject in a single device, wherein said heart rate, respiration, and oxygen saturation of a subject are measured, displayed and shared in a single device.

In some illustrative embodiments, the invention relates to a wearable device for measuring heart rate, respiration, and oxygen saturation of a subject in a single device, wherein said heart rate, respiration, and oxygen saturation of a subject are shared and/or monitored remotely.

In some illustrative embodiments, the invention relates to a wearable device for measuring heart rate, respiration, and oxygen saturation of a subject in a single device, wherein said data processing and analyzing comprises a frequency analysis using a Fourier Transform on data collected over several seconds of time, wherein said frequency is reasonably related to a specific biometric measurement of heart rate and respiration.

In some illustrative embodiments, the invention relates to a wearable device for measuring heart rate, respiration, and oxygen saturation of a subject in a single device, wherein said data processing and analyzing comprises a frequency analysis using a Fourier Transform on data collected over several seconds of time, wherein said frequency is reasonably related to a specific biometric measurement of heart rate and respiration, and wherein said reasonable frequency for heart rate measurement ranges from about 0.4 Hertz (Hz) to about 4 Hz; said reasonable frequency for respiration measurement ranges from about 0.05 Hz to about 1.2 Hz; and said heart rate and respiration are determined by comparing the magnitude of a peak of the Fourier Transform for heart rate and respiration at each frequency to the magnitude of a peak in the Fourier Transform of the accelerometer/gyroscope data in all three axes at each frequency, respectively.

In some illustrative embodiments, the invention relates to a wearable device for measuring heart rate, respiration, and oxygen saturation of a subject in a single device, wherein said data processing and analyzing comprises a frequency analysis using a Fourier Transform on data collected over several seconds of time, and wherein said oxygen saturation in blood of said subject is determined by comparing relative signal strength of red and infrared light collected over several seconds of time.

Methods to measure physiological signals, such as heart rate, using photoplethysmography (PPG) detect changes in the volume of blood flowing through blood vessels due to the rhythmic activity of the heart (J. Allen, Physiol. Meas. 2007, 28(3), p. R1). This volume change is measured by illuminating the capillary bed with a small light source and measuring the amount of light that reflects or passes through the tissue with a photodiode. This technique has been utilized at length in consumer fitness devices for continuous monitoring of heart rate during rest and exercise (D K Spierer, et al., J. Med. Eng. Technol., 2015, 39(5), 264-271). Though heart rate monitoring is undoubtedly beneficial for monitoring general health and activity levels, more sensing capabilities are needed to provide a more holistic picture of human health. Of these additional sensing capabilities, respiration is of particular value since it provides a more comprehensive evaluation of cardiopulmonary activity when coupled with heart rate monitoring (J F Fieselmann, et al., J. Gen. Intern. Med., 1993, 8(7), 354-360). Respiratory monitoring provides additional clinical diagnostic capabilities for diagnosing anomalies such as sleep apnea, hyperventilation, and panic disorders. As such, respiratory rate measurements have extensive clinical utility.

Conveniently, PPG has also been shown to measure respiratory signals in addition to heart rate (P Leonard, et al., Emerg. Med. J. EMJ, 2003, 20(6), 524-525; D Clifton, et al., J. Clin. Monit. Comput., 2007, 21(1), 55-61). This suggests that there is a possibility of monitoring respiratory and heart rate with a single device by analyzing the PPG signal.

In addition to sensing capabilities and detection modalities, the choice of form factor is critical. For heart rate measurements, both chest strap and wrist-worn devices have been developed. However, chest straps are known for their level of discomfort making a wrist-worn device a more attractive form factor. In this report, we detail our on-going development of a wrist-worn PPG device capable of measuring both heart rate and respiration. Our device exceeds the abilities of current commercially available wrist-worn fitness devices, which are able to measure heart rate alone, by demonstrating the ability to measure both heart rate and respiration using additional filtering and signal amplification strategies (D K Spierer, et al., 2015).

A. Feature-Packed

The device is fully-featured to include the main components to perform the physiological monitoring, as well as auxiliary features to give it the capabilities of a watch. The device contains a 9DoF inertial measurement unit, a PCF8523 real-time clock, SD card, 0.66 in' OLED, three user input buttons, an ARM Cortex MO Bluetooth microcontroller, external RAM, a vibration motor, a speaker, fuel gauge for monitoring battery usage, battery charging circuit, and voltage regulator. These components were designed on custom designed printed circuit boards contained within a 42 mm wide×38 mm tall×18mm tall 3D printed enclosure.

B. Pulse and Respiration Sensor Construction

The PPG sensing circuit (FIG. 5B) is primarily composed of a photodiode, a transimpedance amplifier (TIA), and two sets of cascaded active filters. Each set of filters is specifically tuned for monitoring heart rate, which has a frequency range of 0.7 Hz to 3.5 Hz corresponding to 42 beats per minute (BPM) to 210 BPM, and respiratory rate, which has a frequency range of 0.2 Hz to 0.5 Hz corresponding to 12 breaths per minute (BrthPM) to 30 BrthPM, in healthy human adults (E L Eckberg, et al., J. Physiol., 1980, 304(1), 489-502). The TIA converts the current produced by the photodiode to a voltage. This voltage is then sent into each respective set of active filters tuned for heart and respiratory rate monitoring, respectively. The outputs of our PPG sensing circuits are sensed by a microcontroller with a 10-bit analog-to-digital converter. The heart rate circuit is sampled at 11.9 Hz, while the respiration circuit is sampled at 4.0 Hz satisfying Nyquist.

C. Automatic Gain Control

The signal from the photodiode will vary with a number of physiological factors such as skin tone (J Kim, et al. *Sci. Adv.* 2016, 2(8), e1600418). As such, it is necessary to scale the gain of each amplifier stage to avoid saturating the amplifiers. To accomplish this, we employ a dynamic gain control using digitally controlled potentiometers (R3, R14, and R15 in FIG. 5B). Digital potentiometers are variable resistors that can be programmed over a serial interface such as 4-bit I$^2$C bus/SMBus input/output expanders (sub as PCA9536 by NXP Semiconductors N.V.). By employing these digital potentiometers, we can modify the gain of each amplifier stage in software, removing the need for user intervention, and allowing the device to be portable and used in the field.

D. Comparison to Reference Standard

We compared the results from our experimental device to the BioHarness 3 from Zephyr™ Technology. The BioHarness 3 is a U.S.-FDA cleared physiological monitor available in the form of a chest strap. The device collects the electrocardiogram (ECG) signal using fabric electrodes located in the chest strap, and reports both heart and respiratory rates to the user via a convenient mobile application. The data from the BioHarness was exported using the IoTool smartphone application on a ZTE Whirl 2 Z667G Android phone. We chose to compare our device to the BioHarness due to its portability, relative low-cost, and accessible app interface. Furthermore, the device has been validated for accuracy in an earlier study (J H Kim, et al., *Int. J. Sports Med.* 2013, 34(6), 497-501).

E. Device Validation

This study was approved by the Institutional Review Board at Purdue University. As a pilot, we tested our device on two participants, Subject A and Subject B. Prior to participating in the study, both subjects gave oral and written consent. Both subjects were male in the age range of 25-34 years. Other physical characteristics of both subjects are summarized in Table 1 and each subject's skin tone is shown in FIG. 2D. Subjects were allowed to place the experimental device on either hand in accordance with the location each subject usually wears wristwatches. Subjects were instructed to place the device snugly on the wrist, to their own comfort. The device was located about 1-2 inches upwards from the wrist. Subject A placed the device on his non-dominant hand (left), while Subject B placed the device on his dominant hand (right). Each subject also wore the reference standard below the chest about even-level with the diaphragm. Measurements were taken while Subject A sat upright in a chair around a small desk. Subject B was monitored while lying flat on a couch, sleeping.

For initial benchtop validation, the discrete Fourier transform (DFT) was computed in Microsoft Excel using the "Data Analysis ToolPak" toolkit. The DFT was calculated with 128 samples using a rectangular window for both sets of measurements (heart rate and respiration). We then identified the local maxima of the resulting spectra and compared those frequencies to the respiratory and heart rates returned by the commercial device.

TABLE 1

Physical Characteristics of Participating Subjects

| | Subject A | Subject B |
|---|---|---|
| Age Range (years) | 25-34 | 25-34 |
| Gender | Male | Male |
| Height (cm) | 175.3 | 172.7 |
| Weight (kg) | 87.1 | 106.6 |
| Skin Tone | Dark | Medium |
| Dominant Hand | Right | Right |
| Sensor Location | Left Wrist | Right Wrist |
| Testing Position | Seated Upright | Sleeping |

The sampling rates and number of samples were chosen in order to optimize frequency resolution as well as the length of sampling period. In order to collect 128 samples at 11.9 Hz for our heart rate measurements, it is necessary to sample for 11 seconds giving our heart rate determination a refresh rate of 11 seconds and a resolution of 0.09 Hz (5.4 B PM). The frequencies of interest were limited to 0.7 to 3.5 Hz. The conditions for respiratory rate monitoring were determined similarly. Sampling at 4.0 Hz for 128 samples provides a refresh rate of 33 seconds and a frequency resolution of 0.03 Hz (1.8 BrthPM). The frequencies of interest were limited to 0.2 Hz to 0.5 Hz.

To properly compare the results from our device to the BioHarness, a few special considerations had to be made. The reference device returns beat-to-beat heart rate and breath-to-breath respiratory rate measurements, while the experimental device returns the rates over the respective sampling periods. As a result, we averaged the rates reported by the reference device over the same sampling periods as the experimental device.

After benchtop validation, the on-board microcontroller was programmed to compute the DFT on-chip, allowing the device to be completely portable and independent of a computer. The microcontroller was programmed according to the expression for calculating the discrete Fourier transform (DFT) using a rectangular window (J Allen, *IEEE Trans. Acoust. Speech Signal Process*, 1977, 25(3), 235-238). Care was taken to avoid performing trigonometric floating-point calculations on the microcontroller as these are computationally expensive and severely slow down our data processing. Instead, we stored the trigonometric relationships in an array of 128 values mapped as 16-bit unsigned integers between 0 and 1000. Indexing the array instead of computing the exact value of the trigonometric function increased our computing speed extensively. We then limited the calculation of the DFT to the frequencies of interests, namely 0.7 Hz to 3.5 Hz for heart rate measurements and 0.2 Hz to 0.5 Hz for respiratory rate measurements. We were able to calculate the DFT in less than 50 ms compared to 83 seconds when using the exact value of the trigonometric function.

Results and Discussion

Overall, the results from our initial pilot study showed reasonable agreement between the experimental device and the reference device. For each Subject, the error rates were within 3-4 BPM or BrthPM (accounting for rounding) as indicated in FIGS. 3A-3F. For Subject A, the experimental device reported prominent frequency content at 0.28 Hz and 1.40 Hz for heart rate, and 0.12 Hz and 0.28 Hz for respiration. The reference device reported rates of 80 BPM and 16.1 BrthPM during the sampling period, corresponding to 1.40 Hz (84 BPM) and 0.28 Hz (16.8 BrthPM) in the data collected by the experimental device. Furthermore, we observed that for Subject A, the respiratory component could be seen in the heart rate signal (FIGS. 3A and 3B at 0.28 Hz) even before further signal processing was done to amplify the respiratory signal. Data agreement was similar for Subject B. We observed frequency content at 1.21 Hz in the heart rate data and 0.12 Hz and 0.25 Hz in the respiratory data. The reference device reported an average heart rate of 73 BPM and an average respiratory rate of 15.3 BrthPM during the sampling period. This agrees with frequency content at 1.21 Hz (73 BPM) and 0.25 Hz (15 BrthPM) reported by the experimental device.

We do observe the presence of additional frequency content for each Subject and for each measurement that do not appear to be indicative of any physiological signal indicated by the reference device (0.12 Hz in respiratory rate measurements for both subjects and 0.74 Hz in the heart rate spectra for Subject A). We postulate that these additional frequency components could be due to system baseline drift and further investigation is necessary to confirm.

Figure 4A:
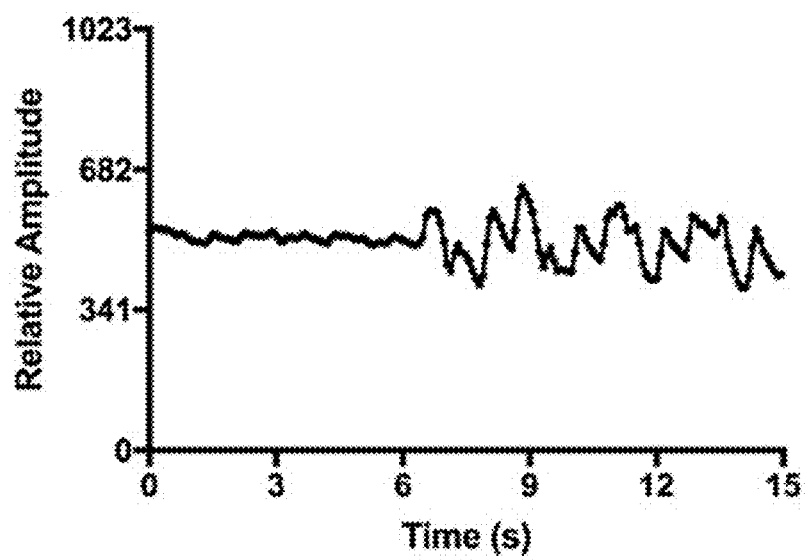
FIG. 4A shows amplitude increase in signal due to activity of auto-gain function. The microcontroller samples the dataset for the full sampling period, then adjusts the gain of the active filters to modulate signal amplitude.
Figure 4B:
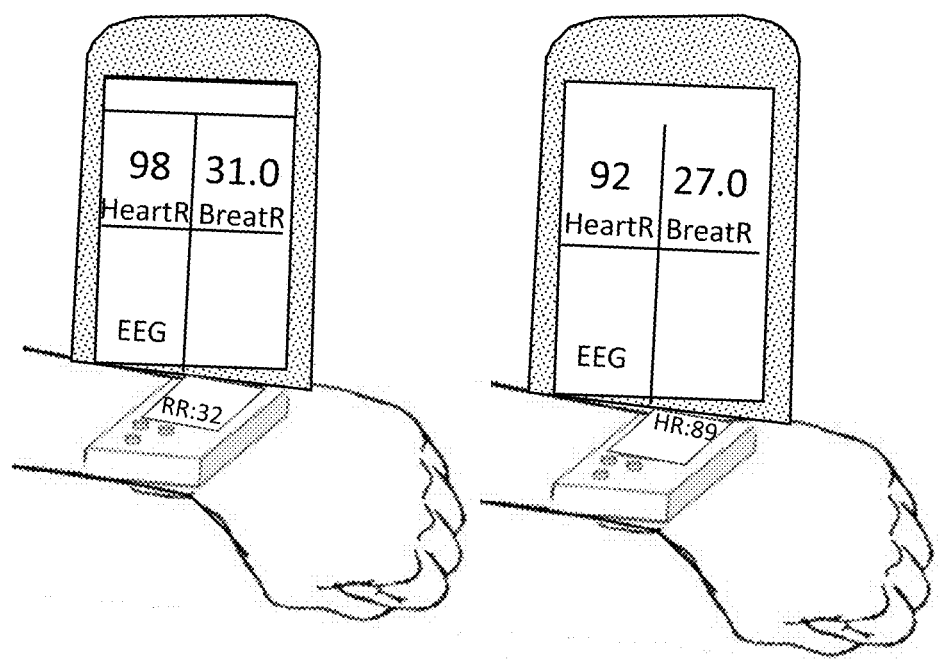
FIG. 4B shows real-time, on-board signal processing of heart and respiratory signals after a very stressful event. The refresh rate of the display is such that heart rate (HR) and respiratory rate (RR) could not be captured in a single photograph at the same time.

Furthermore, we validated our device for untethered collection of data with all processing and determination of physiological rates done on-board (FIGS. 4A and 4B.). Our respiratory rate measurements agreed within 1 BrthPM of the reference standard, while the heart rate measurements agreed within 3 BPM.

To summarize, we have presented a proof-of-concept for accurate measurements of respiration and heart rate on the wrist with a single device. Our device improves upon other wrist-worn PPG sensors, which are only capable of measuring heart rate alone, by demonstrating the ability to detect respiration in addition to heart rate. Future optimization of our algorithms will be done in order to improve the refresh rate of our measurements. We postulate this could be done by sliding our DFT computation across the sampling period. We will also increase the number of human subjects in order to validate the accuracy of our device for all-day wear.

Figure 1:
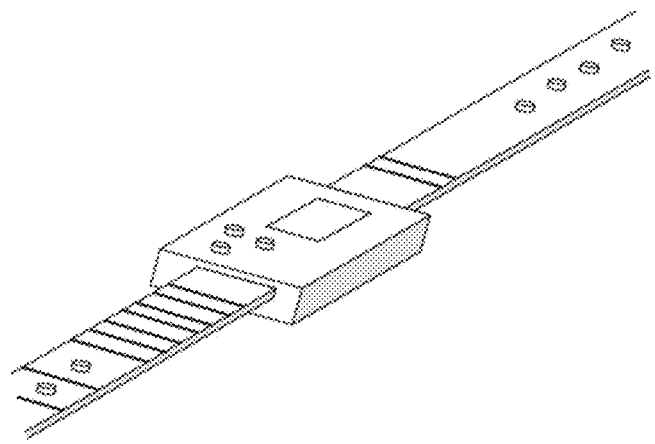
FIG. 1 shows a prototype of a wearable device disclosed herein.

FIG. 1 shows a prototype of a wearable device disclosed herein.

Figure 2A:
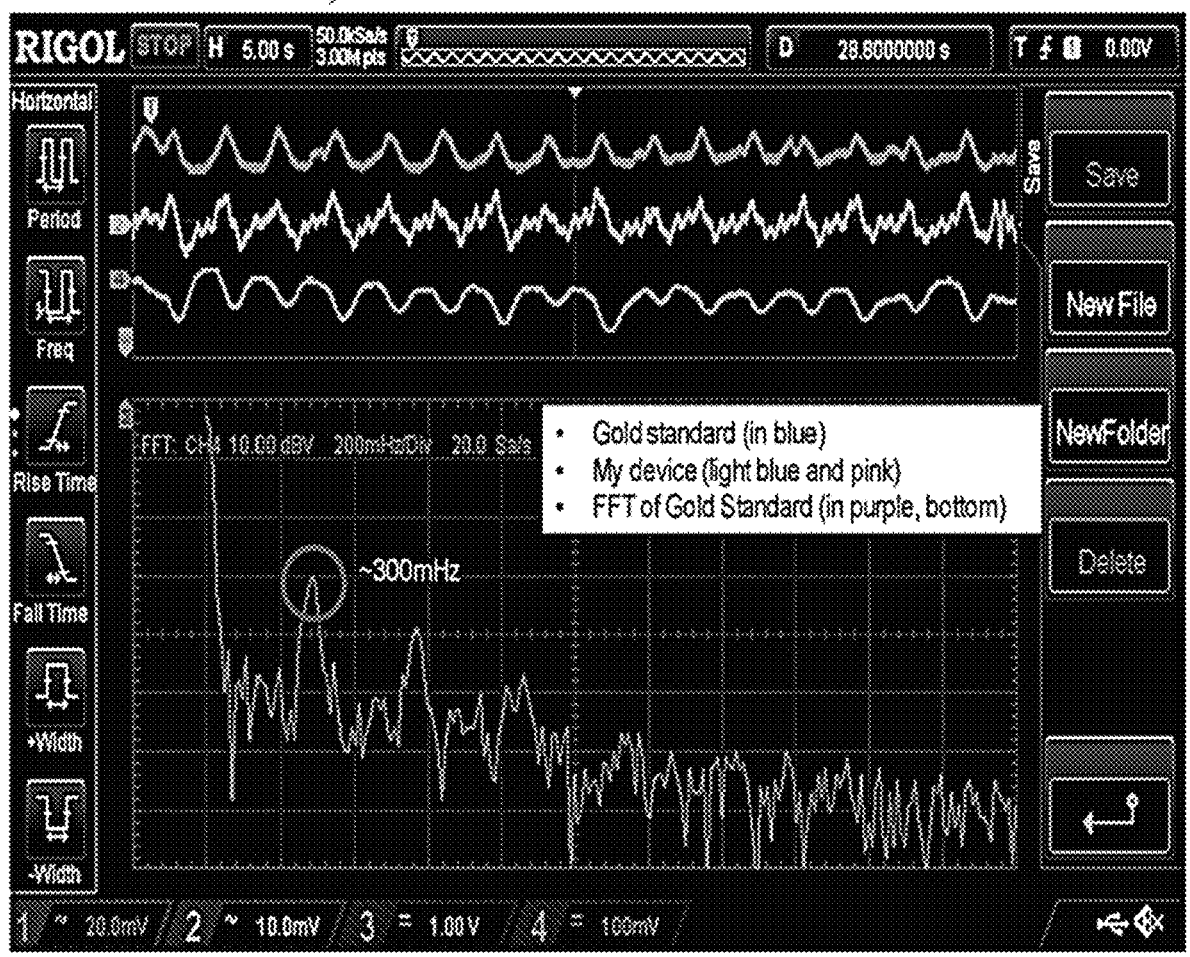
FIG. 2A depicts the waveforms (top panel) the respiration signal in real-time. The dark blue signal is the signal from the gold standard (impedance pneumograph, also known as a pneumatograph or spirograph), the light blue is the signal from our custom device, and the pink signal is also from our custom device after further amplification and filtering. The bottom graph is the fast Fourier Transform (FFT) of the gold standard. This is used to analyze the frequency components of the signal collected from the gold standard in order to calculate respiratory rate. There is a primary frequency component at around 300 mHz. Meaning the respiratory rate is about 0.3 Hz*60=18 breaths per minute.

FIG. 2A depicts the waveforms (top panel) the respiration signal in real-time. The dark blue signal is the signal from the gold standard (impedance pneumograph, also known as a pneumatograph or spirograph), the light blue is the signal from our custom device, and the pink signal is also from our custom device after further amplification and filtering. The bottom graph is the fast Fourier Transform (FFT) of the gold standard. This is used to analyze the frequency components of the signal collected from the gold standard in order to calculate respiratory rate. There is a primary frequency component at around 300 mHz. Meaning the respiratory rate is about 0.3 Hz*60=18 breaths per minute.

Figure 2B:
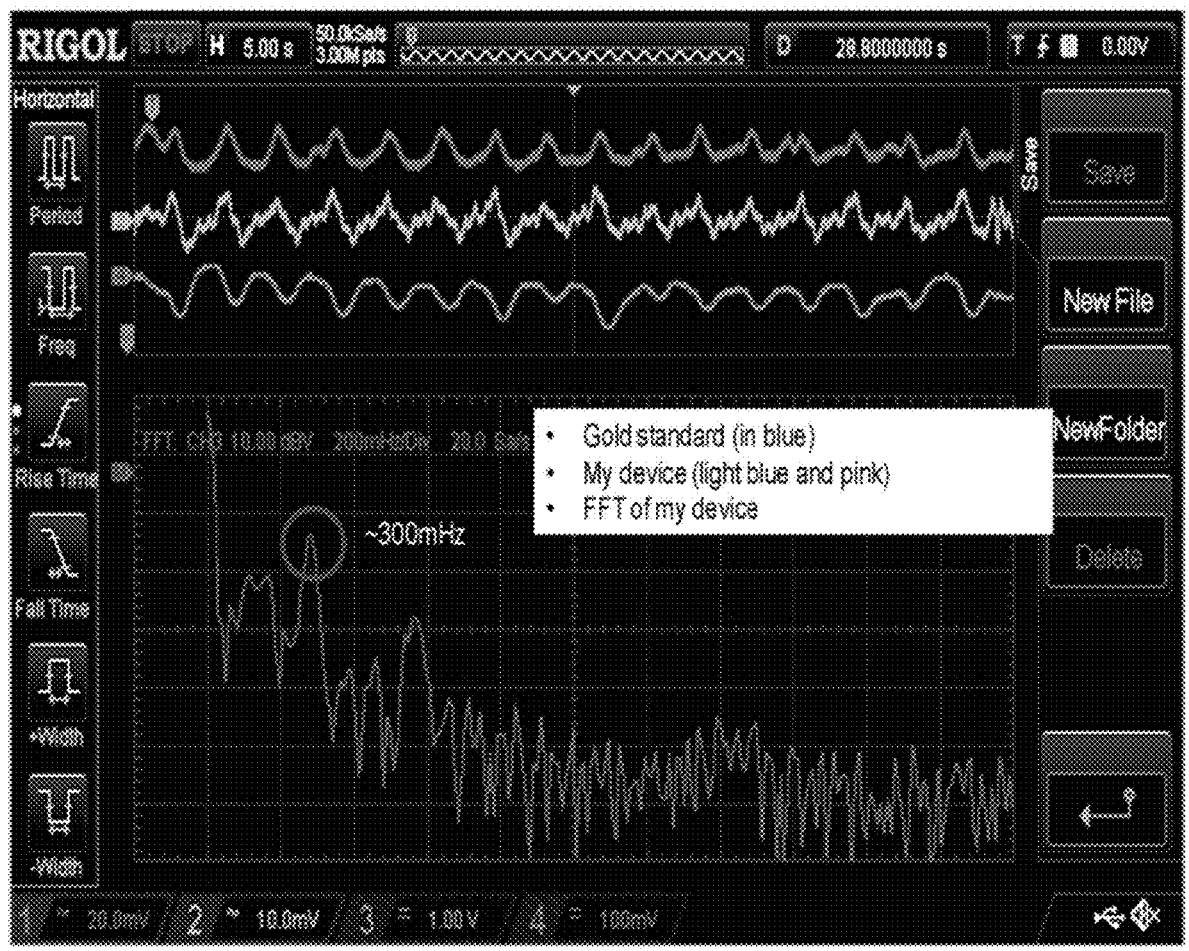
FIG. 2B shows the FFT analysis is now of our custom device. We are comparing the bottom graph of this slide to the bottom graph of slide 3. As you note, there is a primary frequency component at around 300 mHz. This primary frequency component of our custom device (bottom graph slide 4) is identical to the primary frequency component of the gold standard (bottom graph slide 3) meaning that our device was able to detect respiration as well as the gold standard.

FIG. 2B shows the FFT analysis is now of our custom device. We are comparing the bottom graph of this slide to the bottom graph of slide 3. As you note, there is a primary frequency component at around 300 mHz. This primary frequency component of our custom device (bottom graph slide 4) is identical to the primary frequency component of the gold standard (bottom graph slide 3) meaning that our device was able to detect respiration as well as the gold standard.

Figure 2C:
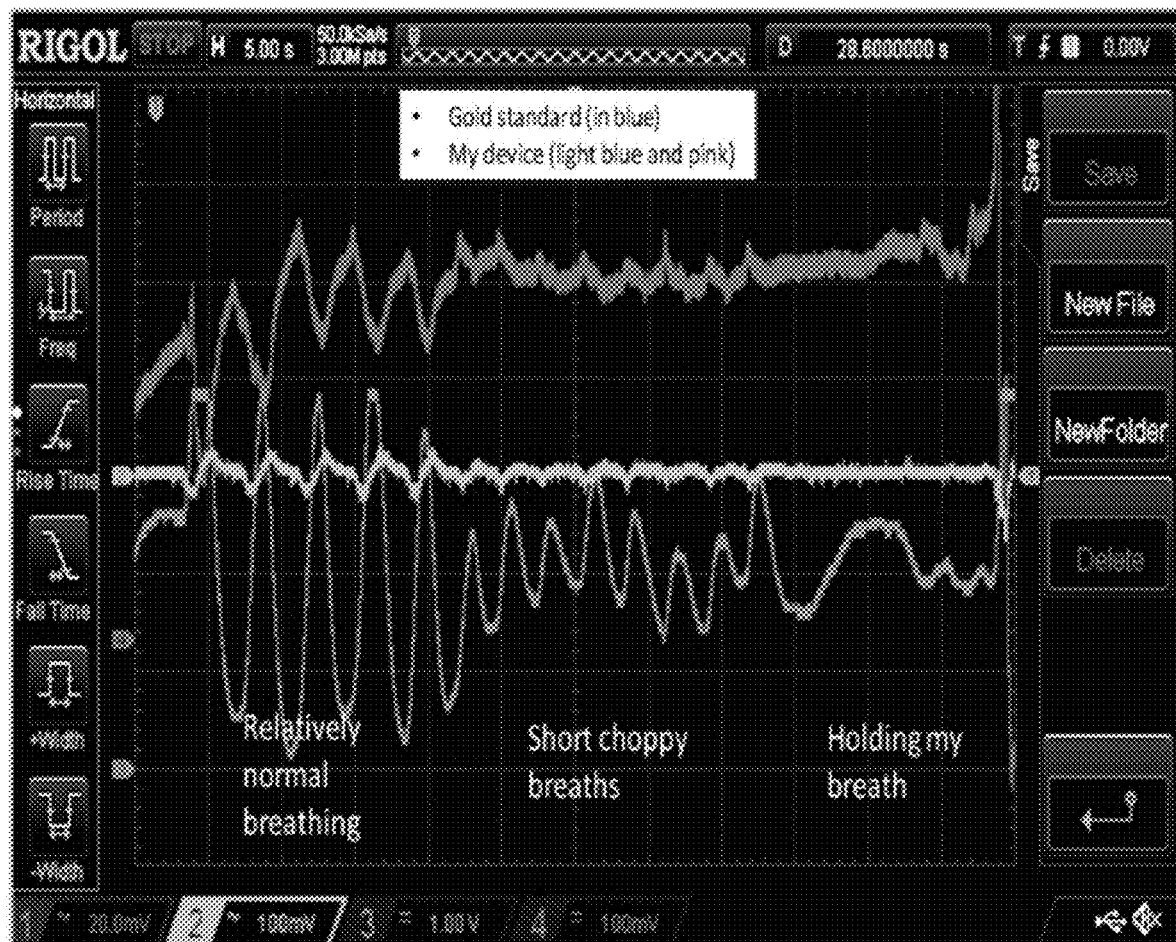
FIG. 2C shows scaled up respiratory patterns as detected by the gold standard (in dark blue), our device (in light blue), and our device again after further amplification and filtering (pink). The sinusoidal patterns measured by our device matches the gold standard for normal breathing, short choppy breaths, and holding one's breath. This slide demonstrates that our device is also able to detect breathing patterns similar to the gold standard.
Figure 2D:
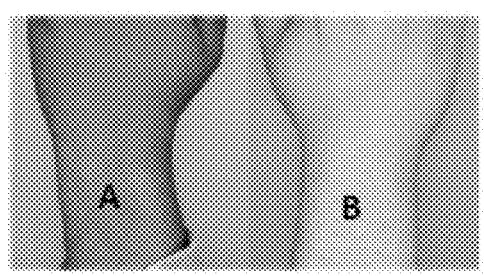
FIG. 2D shows scanned images of subjects' wrists. Images were taken with an Epson Perfection V850 Pro using the Epson Scan Windows application Version 3.9.3.2US with 24-bit color and 600 dpi resolution.

FIG. 2C shows scaled up respiratory patterns as detected by the gold standard (in dark blue), our device (in light blue), and our device again after further amplification and filtering (pink). The sinusoidal patterns measured by our device matches the gold standard for normal breathing, short choppy breaths, and holding one's breath. This slide demonstrates that our device is also able to detect breathing patterns similar to the gold standard.

Figure 3A:
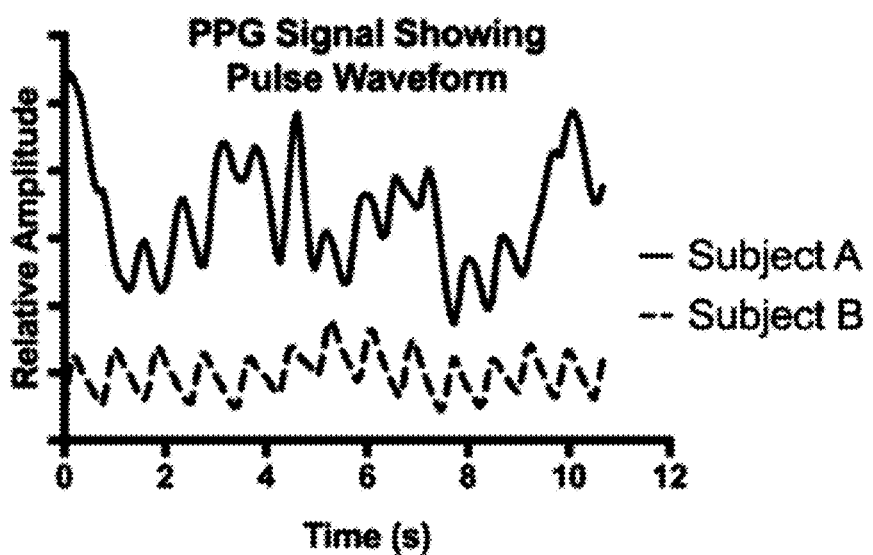
FIG. 3A shows the time domain response of the experimental device to heartbeats for Subjects A and B. We can visibly observe at least 2 frequency components in each signal, one possibly corresponding to heart rate and the other to respiration.

FIG. 3A shows the time domain response of the experimental device to heartbeats for Subjects A and B. We can visibly observe at least 2 frequency components in each signal, one possibly corresponding to heart rate and the other to respiration.

Figure 3B:
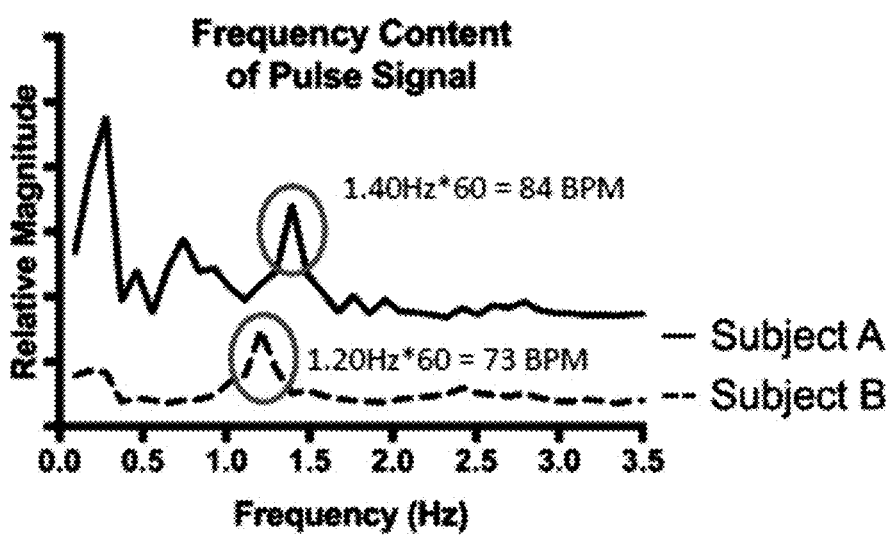
FIG. 3B shows each signal is processed in the frequency domain. Suspected frequency components indicative of heart rate are highlighted.

FIG. 3B shows each signal is processed in the frequency domain. Suspected frequency components indicative of heart rate are highlighted.

Figure 3C:
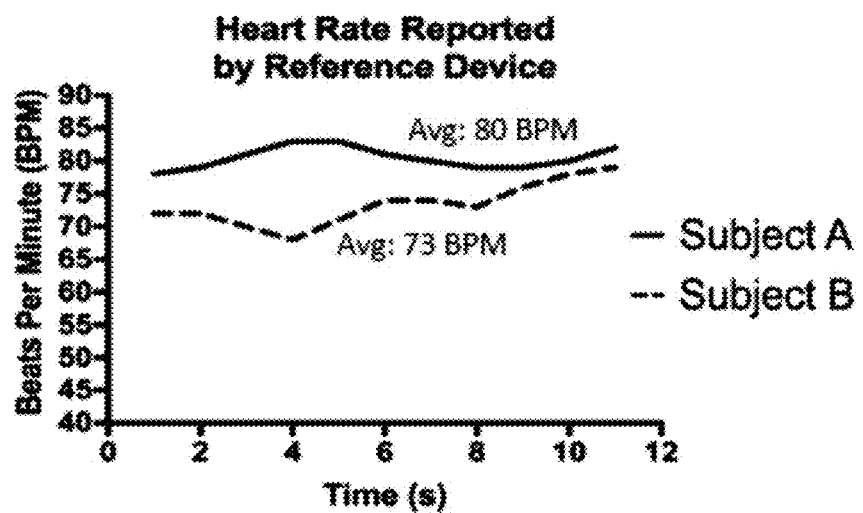
FIG. 3C shows data from the reference device indicates heart rates of 83 BPM and 73 BPM for Subjects A and B, respectively. These rates correspond to frequency components 1.40 Hz for Subject A and 1.21 Hz for Subject B.

FIG. 3C shows data from the reference device indicates heart rates of 83 BPM and 73 BPM for Subjects A and B, respectively. These rates correspond to frequency components 1.40 Hz for Subject A and 1.21 Hz for Subject B.

Figure 3D:
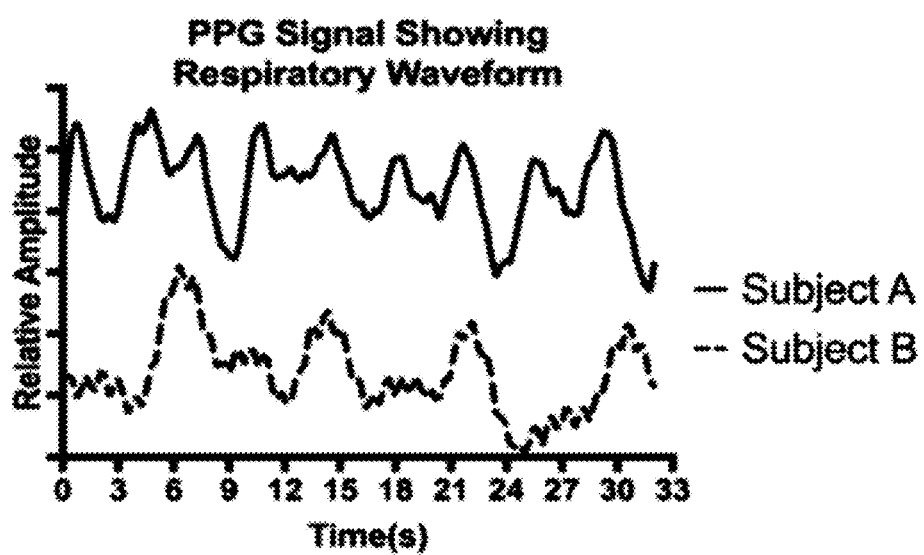
FIG. 3D shows the respiratory signal is shown. We notice slower changes in the signal on the order of several seconds compared to heart rate, which was more on the order of 1 to 1.5 seconds.

FIG. 3D shows the respiratory signal is shown. We notice slower changes in the signal on the order of several seconds compared to heart rate, which was more on the order of I to 1.5 seconds.

Figure 3E:
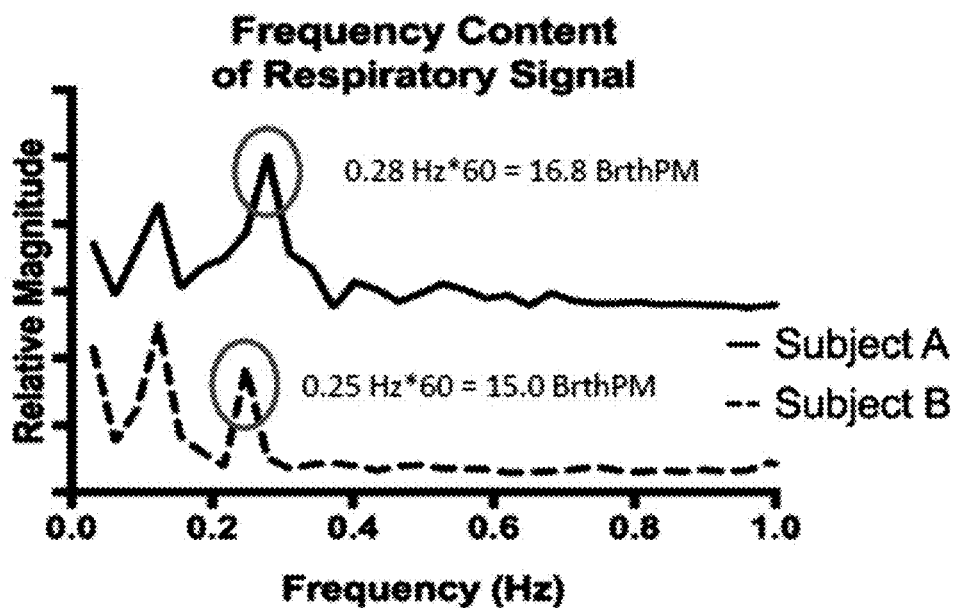
FIG. 3E shows the spectra of the respiration signals are highlighted with two dominant frequency components for each Subject (0.12 Hz and 0.28 Hz for Subject A and 0.12 Hz and 0.25 Hz for Subject B).

FIG. 3E shows the spectra of the respiration signals are highlighted with two dominant frequency components for each Subject (0.12 Hz and 0.28 Hz for Subject A and 0.12 Hz and 0.25 Hz for Subject B).

Figure 3F:
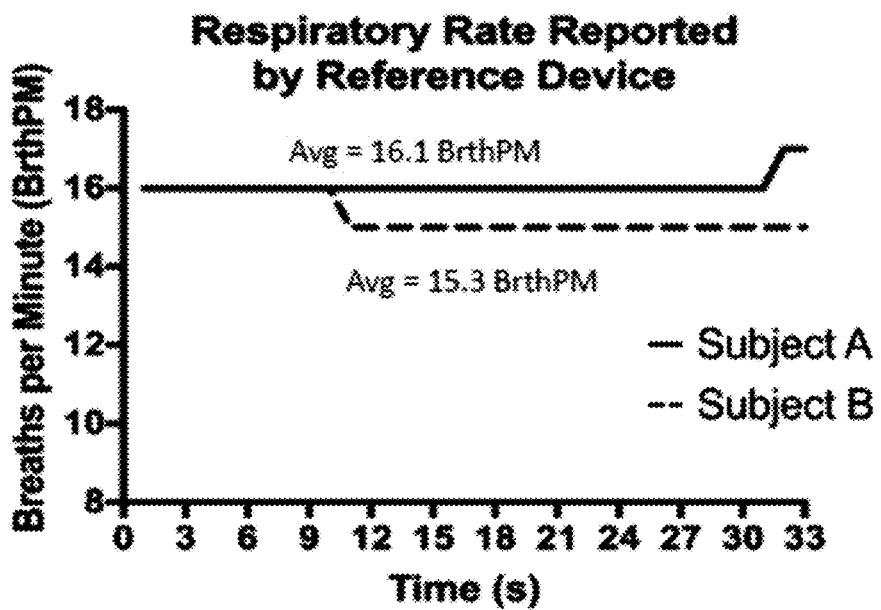
FIG. 3F shows data from the reference device indicates a respiratory rates of 16.1 breathes per minute (BrthPM) for Subject A and 15.3 Hz for Subject B. These rates correspond to peaks at 0.28 Hz (Subject A) and 0.25 Hz (Subject B) for each respective subject.

FIG. 3F shows data from the reference device indicates a respiratory rates of 16.1 BrthPM for Subject A and 15.3 Hz for Subject B. These rates correspond to peaks at 0.28 Hz (Subject A) and 0.25 Hz (Subject B) for each respective subject.

FIG. 4A shows amplitude increase in signal due to activity of auto-gain function. The microcontroller samples the dataset for the full sampling period, then adjusts the gain of the active filters to module signal amplitude.

FIG. 4B shows real-time, on-board signal processing of heart and respiratory signals after a very stressful event. The refresh rate of the display is such that heart rate (HR) and respiratory rate (RR) could not be captured in a single photograph at the same time.

Additionally, there is a few seconds delay between each snapshot resulting in the difference in HR and RR reported by the reference device (viewed on the smartphone), which has a faster refresh rate than the experimental device.

FIG. 5A shows our schematic for our biometric sensor board. In this design, we depict our amplification and filtering scheme for measuring heart rate, respiration, and pulse oximetry. The mathematical calculation of oxygen saturation follows the methods described in the literature as demonstrated with the following formulae shown below (S Sassaroli, et al., *Phys. Med. Biol.* 2004, 49 (14), N255; D. R. Tobler et al., U.S. Pat. No.6,285,896, 4 Sep. 2001; J M Schmitt, *IEEE Transactions on Biomedical Engineering*, 1991, 38 (12), 1194-1203; W. G. Zijlstra, et al., *Clinical Chemistry*, 1991, 37 (9), 1633-1638). We have a dual LED (red and infrared) in which we are able to automatically control the brightness of the LEDs to account for difference in skin tones.

$$S(t) = \frac{AC(t)}{DC(t)}$$

$$R(t) = \frac{\ln(\mathrm{rms}(S(T)_R) + 1)}{\ln(\mathrm{rms}(S(T)_{IR}) + 1)}$$

$$SpO_2(t) = \frac{\varepsilon_{Hb}(\lambda_R) DPF_{R-IR} \varepsilon_{Hb}(\lambda_{IR}) R(t)}{[\varepsilon_{Hb}(\lambda_R) - \varepsilon_{HbO_2}(\lambda_R)] DPF_{R-IR} + [\varepsilon_{HbO_2}(\lambda_{IR}) - \varepsilon_{Hb}(\lambda_{IR})] R(t)}$$

The signal processing for blood oxygenation follows four major steps: a). Discrete Fourier Transform (DFT); b) Peak Detector; c) Spectral Centroid; d) Segmentation.

Discrete Fourier Transform (DFT)

The DFT calculates the frequency content of our signal (RM Rangayyan Biomedical Signal Analysis. John Wiley & Sons, 2015; J W Cooley, et al., IEEE Transactions on Education, 1969, 12 (1), 27-34). This calculation shows how much each frequency contributes to the overall signal by calculating the "magnitude" at each frequency which is a mathematical weight representing how much a particular frequency contributes to the overall signal. We calculate the DFT for our physiological signal (heart rate or respiratory rate) as well as the signals from the accelerometer and gyroscope.

$$X(k) = \sum_{k=0}^{N-1} x(n) * \left[ \cos\left(\frac{2\pi}{N} kn\right) - j * \sin\left(\frac{2\pi}{N} kn\right) \right]$$

where x(n) are the data samples and k=0 to N−1

Peak Detector.

We then employ a peak detector which finds the given frequency that has the largest contribution to the signal by comparing the magnitudes of the DFT calculation at each frequency. We also find the peak frequency in the acceleration and gyroscope data as well. The software then compares the peaks found in the physiological signal to the peaks found in the accelerometer and gyroscope. If the peaks found in the physiological signal are also found in the accelerometer and gyroscope, the frequency is considered noise. The software does this until a unique frequency in the physiological signal that is not represented in the accelerometer or gyroscope data is found.

Spectral Centroid

Once a unique frequency is found for the physiological signal, we calculate the spectral centroid. This is a weighted average of the frequency spectrum around our unique frequency. This allows us to find small variances in our frequency analysis that could be due to small contributions by frequencies around our unique frequency (G J Sandell, Music Percept, 1995, 13(2), 209-246; P N Le, et al., Speech Communication, 2011, 53(4), 540-551; K A Wear, IEEE Transactions on Ultrasonics, Ferroelectrics, and Frequency Control, 2003, 50(4), 402-407).

$$\mathrm{Centroid} = \sum_{k=0}^{N-1} \frac{f_k X(k)}{X(k)}$$

wherein, X(k) is the magnitude of the DFT for each frequency, and f, k are each individual frequency.

The Centroid value represents the most accurate frequency indicative of our physiological value, whether it be heart rate or respiration. To calculate heart rate or respiratory rate, we multiply the centroid by 60 to obtain breaths per minute or beats per minute (depending on which physiological signal we are analyzing) Centroid*60=breaths per minute or beats per minute Segmentation.

The software then re-analyzes the original physiological signal to into different segments. For instance, if we have N samples, the software finds N/4 or N/2 samples that have less noise in them than the entire signal itself. The software does this by observing the level of activity reported by the accelerometer and gyroscope. The software tries to find a period of time within the N samples where the level of activity reported by the accelerometer and gyroscope are low. Once the data is segmented into N/4 or N/2 samples, the software analyzes the segmented data as described above. By doing so, we can perform more accurate frequency analysis by excluding data samples that are too obscured by noise.

FIG. 5B shows schematic of the PPG sensing circuit. The signal from the transimpedance amplifier is sent into two sets of cascaded active filters tuned for heart rate sensing and respiration monitoring, respectively. The outputs of the amplifier stages are sensed by two channels of an on-board IO-bit analog-to-digital converter on a Bluetooth-enabled microcontroller. The signals are processed by the on-board microcontroller. R3, R14, and R15 (highlighted with a dashed box) are digitally controlled potentiometers enabling automatic gain control. Using these potentiometers, the microcontroller can modulate system gain in order to adjust for differences in the optical reflective properties of skin across difference subjects.

FIG. 6 depicts the circuit board design for our biometric sensor board showing how the circuit board is physically laid out in space. Along the left side are the amplifiers and filters. At the center and bottom of the board are the LEDs and light sensor. At the top is the brightness control mechanism for the LEDs.

FIG. 7 shows the back side of the circuit board of FIG. 6

FIG. 8 shows the auxiliary sensor board that contains battery management systems (voltage regulation, battery charging, battery status), a locomotion sensor (accelerometer and gyroscope), a real-time clock (for accurate time keeping), a motor (for user feedback), and a buzzer (also for user tactile feedback).

FIG. 9 shows the circuit board layout for the auxiliary sensor board and where all the components are laid out.

FIG. 10 shows the communications and central processing board that contains our Bluetooth capable central processing unit, an external memory chip (RAM), a screen for displaying information to the user (OLED), an SD card for long term data storage, and buttons for user input. This board handles all the data processing to measure heart rate, respiratory rate, and pulse oximetry. This board is also responsible for controlling all other boards and for sending data to the user.

FIG. 11A depicts the circuit board layout for our communications and central processing board. FIG. 11B shows the back side of the circuit board.

It will be appreciated by persons skilled in the art that the present invention is not limited by what has been particularly shown and described herein. The details of one or more embodiments of the invention are set forth in the accompanying description below. Other features, objects, and advantages of the invention will be apparent from the description and drawings, and from the claims.

The growth of mobile platforms and smart devices has introduced a revolution in healthcare. Despite such growth, premature infants in high-resource neonatal intensive care units (NICU's) remain tied to bulky equipment with numerous wires to perform vital signs monitoring. These tethers limit Kangaroo Mother Care (KMC), a widely recognized standard of care to provide skin-to-skin contact for critical thermal management and mother-baby bonding. Mobile health platforms have the potential to provide valuable monitoring abilities in low resource settings where skin-to-skin contact is substituted for NICU's. To alleviate this limitation, an alternate form of the devices described herein is presented in the present disclosure to measure heart and respiratory rate by analyzing the electrocardiogram (ECG) while seamlessly being integrated into a KMC pouch. A low-processing power, algorithm that analyzes the rhythmic changes in heart rate variability, termed respiratory sinus arrhythmia (RSA), is used in order to determine respiratory rate.

This alternate device uses an AD8226 instrumentation amplifier with a common mode rejection ratio (CMRR) of 120 dB at 60 Hz and 20 dB gain to measure the ECG. The alternate device operates off of a single supply of 3.3V with a gain of 22.6 dB. The system utilizes a groundless, two-lead ECG system by biasing the leads towards ½ $V_{DD}$, making it a simple, compact system. A SAMD21 microcontroller sampling at 500 Hz with a 12-bit analog-to-digital converter processes the incoming signal. A simple digital high pass filter with a cut-off frequency of 67.8 Hz is applied off-board to remove the effect of motion artifacts on the ECG signal. The R-R interval is measured, resulting in instantaneous heart rate for measuring heart rate variability. The sinusoidal oscillations in the heart rate are known as respiratory sinus arrhythmia and can be translated to instantaneous respiratory rate by measuring the time between the heart rate local maximums. The electrodes for this alternate device were placed on the lead author's chest and the electrodes for the reference impedance pneumograph were placed on either side of the chest. Movement trials were conducted by walking back and forth during the trial. Breath holds consisted of stationary, rhythmic breathing with a breath hold of 15 seconds in the middle of the trial.

Using RSA, the algorithm calculates respiratory rate from the ECG measured by Roo LL which consistently follows the trend of the gold standard impedance pneumograph's instantaneous respiratory rate even while moving. The RSA method was also shown to stay consistent with the gold standard's respiratory rate during a breath hold. Thus, this approach allows constant detection of whether a baby is breathing or not regardless if the mother or infant is moving. According to one embodiment, additional sensing modalities, such as blood oxygen and temperature are also included with this alternate device.

Referring to FIG. 12, a block diagram of an alternate heart rate and respiration system 100 according to the present disclosure is provided. The system 100 includes a processor 102 that receives signals from amplified electrodes 104 via an amplification block 106. The processor and other blocks (connections not shown) are powered by a power circuit block 108. The processor then communicates respiration and heart rate information via a communication block 110 which can provide information via a display (not shown) as discussed above.

An actual reduction to practice of the system 100 is provided in FIG. 13, which is a circuit of the system 100. Different blocks of the system 100 are shown in FIG. 13. An AD8226 instrumentation amplifier with a common mode rejection ratio (CMRR) of 120 dB at 60 Hz and 20 dB gain is used to measure the ECG. The system 100 (also referred herein as the Roo LL system) operates off of a single supply of 3.3V with a gain of 22.6 dB. The system utilizes a groundless, two-lead ECG system by biasing the leads towards ½ $V_{DD}$, making it a simple, compact system. A SAMD21 microcontroller (processor 102 ) sampling at 500 Hz with a 12-bit analog-to-digital converter processes the incoming signal. A simple digital high pass filter with a cut-off frequency of 67.8 Hz is applied off-board to remove the effect of motion artifacts on the ECG signal. The R-R interval (i.e., peaks of R-waves as discussed below) is measured, resulting in instantaneous heart rate for measuring heart rate variability. A schematic of a layout of system 100 with actual dimensions is shown in FIG. 14.

The processor 102 of the system 100 carries out a complex operation to determine respiration. The electrodes coupled to the electrodes block 104 provide an EEG signal to the processor via the amplification block 106. The EEG signal includes the well-known PQRST signal from the heart of the subject. The R-wave represents the peak of each heartbeat. A peak detector (operating via hardware or software, as known to a person having ordinary skill in the art) detects the R-waves. The timing between the peaks of the R-waves is then determined to establish intra-periodicity of the heart rate. FIG. 15 is a plot of relative amplitude vs. time in seconds of the PQRST waves with the peaks of the R-waves marked with circles. With the peaks identified, heart rate can be determined by dividing 60 (i.e., beats per minute) by the identified intra-timing between the peaks. Referring to FIG. 16, a graph of relative amplitude is shown vs. time in seconds with intra-timing between R-wave peaks shown as Δt1, Δt2, Δt3, Δt4, and so on with heart rate (HR) calculated based on dividing 60 by each intra-timing between R-wave peaks (i.e., HR1=60/Δt1, HR2=60/Δt2, HR3=60/Δt3, HR4=60/Δt4, and so on). The measured R-R interval (i.e., peaks of R-waves) can be related to instantaneous heart rate for measuring heart rate variability. The sinusoidal oscillations in the heart rate are known as respiratory sinus arrhythmia, as seen in FIGS. 17 and 18 which are complex graphs of heart rate in beats per minute (BPM) and relative amplitude vs. time in seconds, and which can be translated to instantaneous respiratory rate by measuring the time between the heart rate local maxima. The electrodes of the system 100 were placed on a subject's chest and the electrodes for the reference impedance pneumograph (which represents the gold standard) were simultaneously placed on either side of the chest. Movement trials were conducted by walking back and forth during the trial. Breath holds consisted of stationary, rhythmic breathing with a breath hold of 15 seconds in the middle of the trial.

As can be seen from FIG. 17, using RSA to calculate respiratory rate from the ECG measured by the system 100 consistently follows the trend of the gold standard impedance pneumograph's instantaneous respiratory rate even while moving. This calculation is better shown in reference to FIG. 19 which is a graph of heart rate in BMP vs. time in seconds and which shows instantaneous heart rate calculated as discussed above over time. The BPM vs. time graph can be used to obtain the differences in time between consecutive peaks in the ECG signal. Then by dividing that difference in time in the ECG data by 60, yields instantaneous breaths per minute. It should be noted that the intra-peak timing in FIG. 16 are used to obtain heart rate from the ECG (HR=60/dt), whereas the intra-peak timing in FIG. 19 are used to obtain respiration (RR=60/dt) from heart rate (which is over the course of about 5 seconds). This is depicted in FIG. 19. Alternatively, a Fourier transform (e.g., a fast Fourier transform) can be computed of the BPM vs. time which can also yield instantaneous respiratory rate. The ECG detection algorithm or hardware is primarily based on detection of the R-wave since these are the most dominant feature of the ECG. We utilized a dynamic threshold to detect the R-wave. On initialization, the algorithm first collects the ECG signal from the output of the electrodes for 2 seconds, which is sufficient to sample at least one full ECG cycle given a normal, healthy person's slowest possible heart rate of 42 BPM. The algorithm then calculates the standard deviation of the measured signal within the entire 2 seconds and sets a signal amplitude threshold at 1.25 times the standard deviation of the measured signal. After the initial threshold is set, each incoming data point is compared to the threshold in real-time, allowing detection of R-waves in the instant they occur in contrast to other methodologies that only check for R-waves when a programmer-defined number of samples have been collected, thus causing a time lag in the heart rate determination. The threshold is then updated every 2 seconds to adjust for changing ECG amplitudes that could be due to cardiovascular changes or changes in electrode-skin contact that might affect the signal amplitude.

Measuring heart rate variability allows us to utilize RSA, which is the physiological phenomenon of synchronization of heart rate with breathing. When plotted over time, the instantaneous heart rate, as previously calculated, shows peaks when breathing in and valleys when breathing out. This can be converted into respiratory rate using simple analysis in both the time domain and the frequency domain.

The time domain analysis includes a simple derivative method to determine the peaks of instantaneous heart rate. This method is achieved by comparing the current and previous values against each other to find a local maximum. A peak in instantaneous heart rate is found if the following rule is satisfied, $$HR[i] < HR[i-1] > HR[i-2], \text{ or}$$

alternatively $$HR[i] < HR[i-1] < HR[i-2] > HR[i-3] > HR[i-4]$$

where $HR[i]$ is the most recent heart rate value,
$HR[i-1]$ is the previous heart rate value,
$HR[i-2]$ is the heart rate value two heartbeats ago,
$HR[i-3]$ is the heart rate value three heartbeats ago, and
$HR[i-4]$ is the heart rate value four heartbeats ago. Similar to the instantaneous heart rate calculations, respiratory rate can be calculated by measuring the time between peaks in the heart rate. The following equation is used to calculate the instantaneous respiratory rate $$\text{Respiratory Rate} = 60/\text{Time (HR)}$$

where Time (HR) is measured between the current and the previous heart rate value that satisfied the rule stated above.

As discussed above, a Fourier transform can also be used. Thus a second method for respiratory rate detection is analysis in the frequency domain using a fast Fourier transform (FFT). Assuming the maximum breathing rate of a normal human will not exceed 40 breaths per minute, it follows that our signal of interest must reside below 0.67 Hz. This approach is not limited to frequency range of interest and can be expanded. It is only bound by half the frequency of the heart rate. Thus, the original ECG signal can be down sampled to 2 Hz. A 25 second sliding window can then be used to capture data points to be used in the calculation. After performing the FFT, the frequency with the maximum amplitude within our frequency range is taken to be the signal of interest. A peak beyond our frequency range of interest may be viewed as noise. The calculated frequency can then be converted to respiratory rate using the equation $$\text{Respiratory Rate} = f_{FFT} \cdot 60$$

where $f_{FFT}$ is the frequency of interest.

Figure 22:
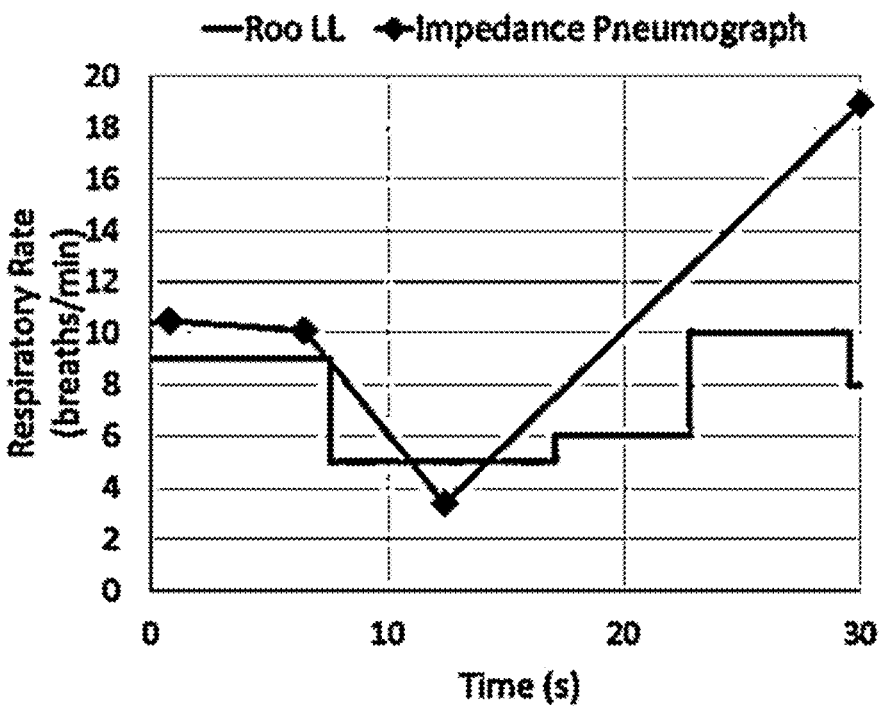

FIG. 20 is another graph of respiratory rate (i.e., breaths per minute) vs. time in seconds comparing the results of the system 100 vs. the gold standard (impedance pneumography). Thus the RSA method is shown to stay consistent with the gold standard's respiratory rate during a breath hold or cessation in breathing. Referring to FIGS. 21 and 22 (where FIG. 21 shows a graph of heat rate in BPM vs. time and FIG. 22 shows the calculated respiratory rate, i.e., breaths per minute vs. time in seconds, both shown with comparison to the gold standard of impedance pneumography), output of the system 100 is shown during breath hold periods with excellent correlation against the gold standard, particularly also as seen in FIG. 28 discussed below. In order to show a quantitative comparison of the correlation between heart rate determined by our device (Roo LL) and the respiration pattern from the impedance pneumography (the gold standard), a statistical comparison was carried out for FIG. 21. The results include a correlation coefficient of $r=0.84$, and p value$<0.05$ (indicating significant correlation), with the actual p-value being 7.4 e-68 (a very small number), indicating superb correlation.

Referring to FIG. 23, two graphs of relative amplitude are shown vs. time in seconds of the PQRST waveform with one shown as an unfiltered signal and the other as a high-pass filtered signal. The filtering allows the respiratory determination to be unaffected by movement of the subject. This immunity is shown in FIG. 24, where the output of the system 100 is shown in comparison with gold standard for respiratory rate in breaths per minute vs. time in seconds over a period of time when the subject is moving. It should be noted that an acceptable correlation between the calculated respiratory rate and the gold standard is within ±2 breaths per minute between the two measures.

Furthermore, the out of system 100 can also provide instantaneous changes in respiratory rate as compared to the gold standard or other commercially available devices, e.g., the BIOHARNESS 3.0. This comparison is shown in FIG. 25, which is a graph of respiratory rate in breaths per minute vs. time in seconds for the three approaches with excellent correlation.

While the electrodes shown in FIG. 14 can be placed on the chest of a subject, the electrodes can also be placed on the back of the subject. Referring to FIG. 26, the respiratory rate in breaths per minute vs. time in seconds is shown in FIG. 26 with electrodes placed on the back of the subject. There continues to be excellent correlation to the gold standard, as seen in FIG. 26.

Additional testing was performed on subjects as shown in FIGS. 27 and 28 which include comparisons of breaths per minute vs. time in seconds based on the output of the system of the present disclosure and as compared to the gold standard for when the subject is walking (FIG. 27) and during breath holds (FIG. 28), again showing excellent tracking as compared to the gold standard of impedance pneumography. Again to show a quantitative comparison, a statistical analysis was carried out for the datasets shown in FIG. 28. The results are based on the correlation between the actual respiratory rates calculated by device of the present disclosure and by the impedance pneumograph (the gold standard) with the subject holding breath from roughly the 90 second mark to the 140 second mark. The correlation coefficient is 0.3798 with a p-value of 0.0171, indicating excellent correlation.

The results provided here show a surprising level of tracking based on instantaneous heart rate calculations and extrapolations of respiratory rate without complicated equipment that are impractical for kangaroo mother care standard for monitoring respiration of an infant. Towards this end, the system of the present disclosure simply uses ECG data based on electrodes placed on the chest or the back of a subject to determine respiration rate.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

Those skilled in the art will recognize that numerous modifications can be made to the specific implementations described above. The implementations should not be limited to the particular limitations described. Other implementations may be possible.

The invention claimed is:

1. A method for measuring and monitoring respiration rate of a subject, comprising the step of
   a) placing a wearable device on a subject for measuring one or more biological parameters of the subject, the wearable device including a biometric sensor board having a photosensor adapted to generate a time-varying signal corresponding to reflectance of red and infrared lights off skin tissue, a locomotion sensor package, comprising a gyroscope and an accelerometer each generating a time-varying motion signal associated with motion with respect to three axes;
   (b) sampling the time-varying photosensor signal and the time-varying motion signals to thereby generate a digitized time-varying photosensor signal and digitized time-varying motion sensor signals;
   (c) applying a Fourier transform to the digitized time-varying photosensor signal and the digitized time-varying motion signals to thereby generate frequency domain spectra associated with magnitudes of the digitized time-varying photosensor signal and the digitized time-varying motion signals;
   (d) detecting peaks of the magnitudes of the spectra of the digitized time-varying photosensor signal and the digitized time-varying motion signals;
   (e) comparing the peaks of magnitudes of the frequency domain spectrum associated with the digitized time-varying photosensor signal with the peaks of magnitudes of the frequency domain spectrum associated with the digitized time-varying motion signals;
   (f) identifying a peak present in the frequency domain spectrum associated with the digitized time-varying photosensor signal which is not present in the peaks of magnitudes of the frequency domain spectrum associated with the digitized time-varying motion signals;
   (g) multiplying the frequency associated with the identified peak by 60 to thereby generate activity per minute to thereby process respiration rate data; and
   communicating the processed respiration rate data by displaying said processed respiration rate on the wearable device.

2. The method of claim 1, further comprising: obtaining and processing of electrocardiogram (ECG) data including:
   i) parsing the ECG data into a P-wave, a Q-wave, an R-wave, an S-wave, and a T-wave;
   ii) detecting peaks of the parsed ECG data;
   iii) determining the intra-timing between the detected R-wave peaks;
   iv) dividing 60 by the determined intra-timing to generate instantaneous heart rate; and
   v) assigning instantaneous respiration rate as the instantaneous heart rate.

3. The method of claim 2, wherein the peak detection is via software.

4. The method of claim 2, wherein the peak detection is via hardware.

5. The method of claim 1, wherein the subject is moving.

6. The method of claim 5, wherein the subject is walking.

7. The method of claim 1, wherein the subject has erratic breathing.

8. The method of claim 7, wherein the subject holds his/her breaths.

9. The method of claim 1, further comprising:
filtering the ECG data prior to the processing step.

10. The method of claim 9, wherein the filtering is with a high-pass filter.

* * * * *